United States Patent
Neal

(10) Patent No.: US 6,642,274 B1
(45) Date of Patent: Nov. 4, 2003

(54) METHODS AND COMPOSITIONS FOR PREVENTING AND TREATING PROSTATE DISORDERS

(76) Inventor: Gary W. Neal, 4701 Guinn Rd., Knoxville, TN (US) 37931

(*) Notice: Subject to any disclaimer, the term of this patent is extended or adjusted under 35 U.S.C. 154(b) by 154 days.

(21) Appl. No.: 09/658,180

(22) Filed: Sep. 8, 2000

Related U.S. Application Data

(60) Provisional application No. 60/152,903, filed on Sep. 9, 1999.

(51) Int. Cl.$^7$ .................... A01N 37/08; C07C 177/00
(52) U.S. Cl. .................... 514/573; 560/121; 562/503
(58) Field of Search ........................ 514/573

(56) References Cited

U.S. PATENT DOCUMENTS

| | | |
|---|---|---|
| 4,474,813 A | 10/1984 | Neri et al. |
| 5,480,640 A | 1/1996 | Morales et al. |

FOREIGN PATENT DOCUMENTS

| | | |
|---|---|---|
| DE | 197 39 693 A1 | 3/1981 |
| DE | 3408260 A1 | 9/1985 |
| DE | 195 40 642 A1 | 5/1997 |
| EP | 0 037943 | 10/1981 |
| WO | WO 97/10842 | 3/1997 |
| WO | WO 97/34595 | 9/1997 |
| WO | WO 98/29101 | 7/1998 |
| WO | WO 99/09970 | 3/1999 |
| WO | WO 99/56739 | 11/1999 |

OTHER PUBLICATIONS

Intravesical Bacillus Calmette–guerin for Treatment of Superficial Transitional Cell Carcinoma of the Prostatic Urethra in Association with Carcinoma of the Bladder; Paul F. Schellhammer, et al., *The Journal of Urology*, vol. 153, No. 1, Jan. 1995, pp. 53–56.

Immunotherapy of Bladder Cancer, Unyime O. Nseyo, et al., *Seminars in Surgical Oncology*, vol. 13, No. 5, 1997, pp. 342–349.

Effect of in Vivo Administration of Prostaglandins and Interferon on Natural Killer Activity and on B–16 Melanoma Growth in Mice, Enrico Garaci, et al, *Cellular Immunology*, vol. 106, No. 1, 1987, pp. 43–52.

Synergistic Inhibition of Human Marrow Granulocyte–Macrophage Progenitor Cells by Prostaglandin E and Recombinant Interferion–α, –β, and –γ and an Effect Mediated by Tumor Necrosis Factor, Louis M. Pelus, et al., *The Journal of Immunology*, vol. 140, No. 2, Jan. 15, 1988, pp. 479–484.

The Dual Interaction of Prostaglandin $E_2$ ($PGE_2$) and Interferon (IFN) on NK Lytic Activation: Enhanced Capacity of Effector–Target Lytic Interactions (Recycling) and Blockage of Pre–NK Cell Recruitment, Stephan R. Targan, *The Journal of Immunology*, vol. 127, No. 4, Oct. 1981, pp. 1424–1428.

Atul Maini, et al; Comparative Pathology of Benign Prostatic Hyperplasia and Prostate Cancer; in vivo 11:293–300 (1997).

Neil H. Bander, et al; MHC Class I and II Expression in Prostate Carcinoma and Modulation by Interferon–Alpha and–Gamma; The Prostate 33:233–239 (1997).

George Blackledge, et al, Bicalutamide: a new antiandrogen for use in combination with castration for patients with advanced prostate cancer; Anti–Cancer Drugs 1996, 7, pp. 27–34.

G.R.P. Blackledge, et al; Casodex™ (Bicalutamide): Overview of a New Antiandrogen Developed for the Treatment of Prostate Cancer; European Urology 1997;31 (suppl 2):30–39.

R.L. Byrne, et al; Peptide growth factors in the prostate as mediators of stromal epithelial interaction; British Journal of Urology (1996), 77, 627–633.

Linda Carroll; New marker may signal future risk of prostate cancer; Medical Tribune Oncology, Feb. 19, 1998, p. 14.

June M. Chan, et al, Plasma Insulin–Like Growth Factor–I and Prostate Cancer Risk: A Prospective Study; Science, vol. 279, Jan. 23, 1998, pp. 563–565.

Stanley S.C. Chang, et al; Transrectal ultrasound guided manipulation of the canine prostate with minimum intervention; Laboratory Animals (1997) 31, 219–224.

Y Chen and M Hughes–Fulford; Prostaglandin $E_2$ and the protein kinase A pathway mediate arachidonic acid induction of c–fos in human prostate cancer cells; British Journal of Cancer (2000) 82, (12), 2000–2006.

Danai D. Daliani, et al; The Results of a Phase II Randomized Trial Comparing 5–Fluorouracil and 5–Fluorouracil Plus □–Interferon: Observations on the Design of Clinical Trials for Androgen–Independent Prostate Cancer; The Journal of Urology, vol. 153, 1587–1591, May 1995.

R. De Coster, et al; P450–Dependent Enzymes as Targets for Prostate Cancer Therapy; J. Steroid Biochem, Molec. Biol. vol. 56 Nos. 1–6, pp. 133–143, 1996.

T.M. de Reijke; Intermittent androgen deprivation in advanced prostate cancer; Urol Res (1997) 25 [Suppl 2]: S63–S66.

(List continued on next page.)

Primary Examiner—Paul J. Killos
(74) Attorney, Agent, or Firm—Rothwell, Figg, Ernst & Manbeck, P.C.

(57) ABSTRACT

The present invention relates to methods, compositions, devices and kits for the prevention and treatment of prostate disorders in mammals, including, but not limited to, benign prostatic hypertrophy, carcinoma of the prostate, prostadynia, prostatitis, and chronic prostatitis. The present invention provides methods for preventing and treating prostate disorders in mammals by administration of a therapeutic compound to mucosal membranes in the lower urinary tract of the mammal. The present invention also provides devices for administering a therapeutic compound to mucosal membranes in the lower urinary tract of the mammal.

19 Claims, 7 Drawing Sheets

OTHER PUBLICATIONS

Rolf H. Drivdahl, et al; IGF–Binding Proteins in Human Prostate Tumor Cells: Expression and Regulation by 1,25–Dihydroxyvitamin $D_3$; The Prostate 26:72–79 (1995).

Robert A. Edelstein, et al; Implications of Prostate Micrometastases in Pelvic Lymph Nodes: An Archival Tissue Study; Urology 47 (3), 1996.

Simon J. Hall and Timothy C. Thompson; Spontaneous but not experimental metastatic activities differentiate primary tumor–derived vs metastasis–derived mouse prostate cancer cell lines; Clin. Exp. Metastasis, 1997, 15, 630–638.

Amy C. Hobeika, et al; IFN$\alpha$ induces the expression of the cyclin–dependent kinase inhibitor in human prostate cancer cells; Oncogene (1997) 14, 1165–1170.

Mutsushi Kawakita, et al; Effect of Canarypox Virus (ALVAC)–Mediated Cytokine Expression on Murine Prostate Tumor Growth; Journal of the National Cancer Institute, vol. 89, No. 6, Mar. 19, 1997, pp. 428–436.

Lester A. Klein and Jeffrey S. Stoff; Prostaglandins and the Prostate: An Hypothesis on the Etiology of Benign Prostatic Hyperplasia; The Prostate 4:247–251 (1983).

Laurence N. Kolonel; Nutrition and prostate cancer; Cancer Causes and Control 1996, 7, pp. 83–94.

E. N. Lalani, Prostate cancer; the interface between pathology and basic scientific research; seminars in Cancer Biology, vol. 8, 1997: pp. 53–59.

Raymond J. Leveillee, et al; Enhanced Radiofrequency Ablation of Canine Prostate Utilizing a Liquid Conductor: The Virtual Electrode; Journal of Endourology, vol. 10, No. 1, Feb. 1996, pp. 5–11.

David M. Lubaroff, et al; Survival of Human Prostate Carcinoma, Benign Hyperplastic Prostate Tissues, and IL–2–Activated Lymphocytes in SCID Mice; The Prostate 27:32–41, (1995).

C.S. Mantzoros, et al; Insulin–like growth factor 1 in relation to prostate cancer and benign prostatic hyperplasia; British Journal of Cancer (1997) 76(9), 1115–1118.

Y. Nakajima, et al; Effect of tumor necrosis factor–$\alpha$ and interferon–y on the growth of human prostate cancer cell lines; Urol Res (1995) 23:205–210.

Yosuke Nakajima, et al; TNF–Mediated Cytotoxicity and Resistance in Human Prostate Cancer Cell Lines; The Prostate 29:296–302 (1996).

Joel B. Nelson, et al; Endothelin–1 Production and Decreased Endothelin B Receptor Expression in Advanced Prostate Cancer; Cancer Research 56, 663–668, Feb. 15, 1996.

Stephen R. Plymate, et al; The Effect on the Insulin–Like Growth Factor System in Human Prostate Epithelial Cells of Immortalization and Transformation by Simian Virus–40 T Antigen; Journal of Clinical Endocrinology and Metabolism, vol. 81, No. 10 (1996), 3709–3716.

K. Purvis, et al; Hormonal Activation of the Adenylyl Cyclases of the Rat and Human Prostate Gland; The Prostate 8:11–24 (1986).

Lisa Pylkkänen, et al; Animal Models for the Preneoplastic Lesions of the Prostate; European Urology 1996; 30:243–248, 243–248.

Klaus Rembrink, et al; Orthotopic Implantation of Human Prostate Cancer Cell Lines: A Clinically Relevant Animal Model for Metastatic Prostate Cancer; The Prostate 31:168–174 (1997).

Bruce J. Roth; New Therapeutic Agents for Hormone–Refractory Prostate Cancer; Seminars in Oncology, vol. 23, No. 6 Suppl 14 (Dec.), 1996: pp. 49–55.

Julia A. Sensibar; Analysis of Cell Death and Cell Proliferation in Embryonic Stages, Normal Adult, and Aging Prostates in Human and Animals; Microscopy Research and Technique 30:342–350 (1995).

E. R. Sherwood and C. Lee; Epidermal growth factor–related peptides and the epidermal growth factor receptor in normal and malignant prostate; World Journal of Urology (1995) 13:290–296.

Mitchell H. Sokoloff, et al; In Vitro Modulation of Tumor Progression–Associated Properties of Hormone Refractory Prostate Carcinoma Cell Lines by Cytokines; American Cancer Society 1996, 1862–1872.

Ed Sussman; Drug used for enlarged prostates said to treat baldness; America Academy of Dermatology, Apr. 17, 1997 p. 23.

Johannes V. Swinnen, et al; Androgens Stimulate Fatty Acid Synthase in the Human Prostate Cancer Cell Line LNCaP[1] Cancer Research 57, 1086–1090, Mar. 15, (1997).

Steven E. Nunn, et al; Regulation of Prostate Cell Growth by the Insulin–Like Growth Factor Binding Proteins and Their Proteases; Endocrine, vol. 7, No. 1, 115–118, Aug. 1997.

Håkan Wennbo, et al; Transgenic Mice Overexpressing the Prolactin Gene Develop Dramatic Enlargement of the Prostate Gland; Endocrinology, vol. 138, No. 10, 1997, 4410–4415.

J.R. Gingrich and N.M. Greenberg; A Transgenic Mouse Prostate Cancer Model; Toxicology Pathology ISSN:0195–6233; vol. 24, No. 4, 1996, 502–504.

Kenneth J. Pienta, et al; Inhibition of Spontaneous Metastasis in a Rat Prostate Cancer Model by Oral Administration of Modified Citrus Pectin; Journal of the National Cancer Institute, vol. 87, No. 5, Mar. 1, 1995.

George Sigounas, et al; dl–$\alpha$–Tocopherol Induces Apoptosis in Erythroleukemia, Prostate, and Breast Cancer Cells, Nutrition and Cancer, 28(I), 30–35, 1997.

Graham Giles and Paul Ireland, Diet, Nutrition and Prostate Cancer; Int. J. Cancer: Supplement 10, 13–17 (1997).

PVP Jen and JS Dixon: Development of peptide–containing nerves in the human fetal prostate gland, 169–179 (1995).

S Kasi, et al.: Hepatocyte growth factor is a paracrine regulator of rat prostate epithelial growth; Biochemical and Biophysical Res Commun; 646–652 (1996).

P. Langenstroer; Endothelin–1 in the human prostate: tissue levels, source of production and isometric tension studies; Journal of Urology: 459 (1993).

Carlos Maramag, et al; Effect of Vitamin C on Prostate Cancer Cells in Vitro: Effect on Cell Number, Viability and DNA Synthesis; The Prostate 32:188–195 (1997).

Massimo Maffezzini, et al; Salvage Immunotherapy with Subcutaneous Recombinant Interleukin 2 (rIL–2) and Alpha–Interferon (AAA–IFN) for Stage D3 Prostate Carcinoma Failing Second–Line Hormonal Treatment; The Prostate 28:282–286 (1996).

Michael Hoey, et al; Transurethral Prostate Ablation with Saline Electrode Allows controlled Production of larger Lesions than conventional Methods; Journal of Endourology; 279–284 (Aug. 11, 1997).

Alvaro Morales, et al; Intralesional Administration of Biological Response Modifiers in the Treatment of Localized Cancer of the Prostate: A Feasibility Study; Urology, 50 (4), 1997, 495–502.

G. Murphy, et al: Phase I Clinical trial: T–Cell Therapy for Prostate Cancer Using Autologous Dendritic Cells Pulsed with HLA–A0201–Specific Peptides from Prostate–Specific Membrane Antigen Prostate; 1996, 371–380.

Abraham Nomura, et al; Serum Micronutrients and Prostate Cancer in Japanese Americans in Hawaii; Cancer Epidemiology, Biomarkers & Prevention, vol. 6, 487–491, Jul. 1997.

M. Paugert–Braquet, et al;Effect of the Lipidosterolic Extract of Serenoa repens (Permixion) and its Major Components on Basic Fibroblast Growth Factor–Induces Proliferation of Cultures of Human Prostate Biopsies; European Urology, 340–347, 1998.

D.M. Peehl, et al; The insulin–like growth factor system in the prostate; World Journal of Urology, 306–311, 1995.

K Pienta, et al; Epidemiology of prostate cancer:; Molecular and environmental clues; Urology, 1997.

N. Shinohara, et al; 5–Fluorouracil and Alpha–2a Interferon in Patients with Hormone–Refractory Prostate Cancer. Japanese Journal of Urology; Oct., 1995. 1557–1562.

C. Sivinski, et al; Modulation of Tumor–Associated Antigen Expression on Human Pancreatic and Prostate Carcinoma Cells in vitro by a– and g–interferonsJournal of Immunotherapy with Emphasis on Tumor Immunology; Oct., 1995. 156–165.

I.M. Thompson, et al; Chemoprevention of Prostate Cancer: The Prostate Cancer Prevention Trial. Prostate; 1997. 217–221.

H.D. Vlajinac, et al; Diet and Prostate Cancer: a Case–Control Study; European Journal of Cancer, vol. 33, No. 1, pp. 101–107, 1997.

G. Yang, et al; Transforming growth factor b1 transduced mouse prostate reconstitutions: II. Induction of the apoptosis by Doxazosin; Prostate, vol. 33, No. 1, pp. 157–163, 1997.

Ian Yip, et al; Nutritional Approaches to the Prevention of Prostate Cancer Progression; Advances in Experimental Medicine and Biology; 1996, 173–181.

T.M.A. ElAtter, et al; Inhibiton of growth in oral squamous carcinoma cells by cyclopentenone prostaglandins; prostaglandins, Leukotrienes & Essential Fatty Acids; 1997, 461–465.

Myriam Gorospe, et al; Protective Role of p21(Waf1/Cip1) against Prostaglandin A2–Mediated Apoptosis of Human Colorectal Carcinoma Cells; Molecular and Cellular Biology; 1996, 762–770.

Myriam Gorospe, et al; Inhibition of G1 Cyclin–Dependent Kinase Activity during Growth Arrest of Human Breast Carcinoma Cells by Prostaglandin; Molecular and Cellular Biology; Mar. 1996, p762–770.

J. Kaneti, et al; Prostaglandin E2 Effects the Tumor Immune Response in Prostatic Carcinoma; Journal of Urology; 1981, 65–70.

C.M. Kunzle, et al; A Comparative Histopathological study of the influence of chemo–and radiotherapy on human prostatic carcinoma grown in nude mice; Experimental and Toxicologic Pathology; 1997, 249–252.

G.R. Kunha, et al; Smooth muscle–epithelial interactions in normal and neoplastic prostatic development; Acta Anatomica; 1966, 63–72.

B.K. Choe, et al; Natural Killer Cell Activity of Prostatic Cancer Patients; Cancer Investigation; 1987, 285–291.

Monika Eichholzer, et al; Prediction of Male Cancer Mortality by Plasma Levels of Interacting Vitamins: 17–Year Follow–Up of the Prospective Basel Study; International Journal of Cancer; Apr. 10, 1996. 145–150.

Murray Korc, et al; Role of Growth Factors in Pancreatic Cancer; Surgical Oncology Clinic of North America; 1998. 25–41.

Ruth E. Patterson, et al; Vitamin supplements and cancer risk: the epidemiologic evidence; Cancer Causes and Control; Sep. 1977, 786–802.

O. Rokhlin and M. Cohen; Soluble forms of CD44 and CD54 (ICAM1) cellular adhesion molecules are released by human prostatic cancer cell lines; Cancer Letters; Oct. 1, 1996. 29–35.

David P. Rose; Dietary fatty acids and cancer; American Journal of Clinical Nutrition; Oct. 1997, 998S–1003S.

D.M.A. Watson, et al; Prostaglandins in human mammary cancer; British Journal of Cancer; Apr. 1984, 459–464.

G.S. Gerber; The role of Urodynamic study in the elevation and management of men with lower urinary tract symptoms secondary to benign prostatic hyperplasia; Urology; 1998, 668=675.

D.M.A. Watson, et al; Prostaglandins in human mammary cancer; British Journal of Cancer; Apr. 1984, 459–464.

Charles Hoyle, et al; Effects of vitamin E deficiency on autonomic neuroeffector mechanisms in the rat Caecum, vas deferens and urinary bladder; Journal of Physiology; 1995, 773–786.

J. Haylor, et al; Urine pH and the Relationship Between Urine Flow and Urinary Prostaglandin E Excretion in the Rat; Journal of Endocrinology; Feb. 1986, 247–253.

T. Morita, et al; Effects of Prostaglandins E1, E2, and F2a on Contracility and cAMP an cGMP Contents in Lower Urinary Tract Smooth Muscle; 1994, 200–203.

S. Palea, et al; Pharmacological Characterization of Thromboxane and Prostanoid Receptors in Human Isolated Urinary Bladder; 1998, 865–872.

Ulf Ulmsten; Prostaglandins and the Urinary Tract; Acta Obstet Gynecol Scand; 1983, 55–58.

G. Wagner, et al; Is Prostaglandin E2 Really of Therapeutic Value for Postoperative Urinary Retention? Results of a Prospectively Randomized Double–Blind Study; American Journal of Obstetrics and Gynecology; Feb. 1, 1985, 375–379.

Manabu Kitazawa, et al; Interactions between Vitamin E Homologues and Ascorbate Free Radicals in Murine Skin Homogenates Irradiated with Ultraviolet Light; Photochemistry and Photobiology; 1997, 355–365.

Kouji Ohno, et al; Characterization of the Transport System of Prostaglandin A2 in :L–1210 Murine Leukemia Cells; Biochemical Pharmacology; Apr. 27, 1993, 661–670.

Joachim Wubert, et al; Simultaneous Solid Phase Extraction, Derivatization and Gas Chromatographic Mass Spectrometric Quantification of Thromboxane and Prostacyclin Metabolites, Prostaglandins, and Isoprostanes in Urine; Analytical Chemistry; 1997, 2143–2146.

Hiroshi Yamamoto, et al;Prostaglandin E2–Induced Activation of Adenosine 3'–5' Cyclic Monophosphate–Dependent Protein Kinases of a Murine Macrophage–Like Cell Line (P388D1); The Journal of Immunology; Nov. 15, 1987, 3416–3421.

C.C. Chang, et al; 15–Hydroxyprostaglandin Dehydrogenase Activity in the Lower Genitrourinary Tract; British Journal of Urology; 1991, 579–581.

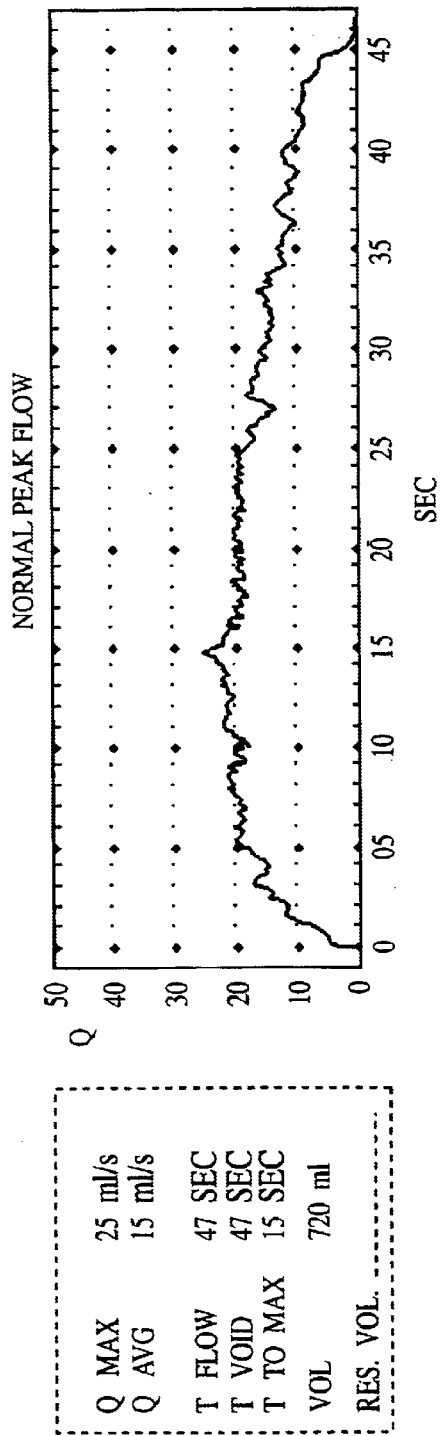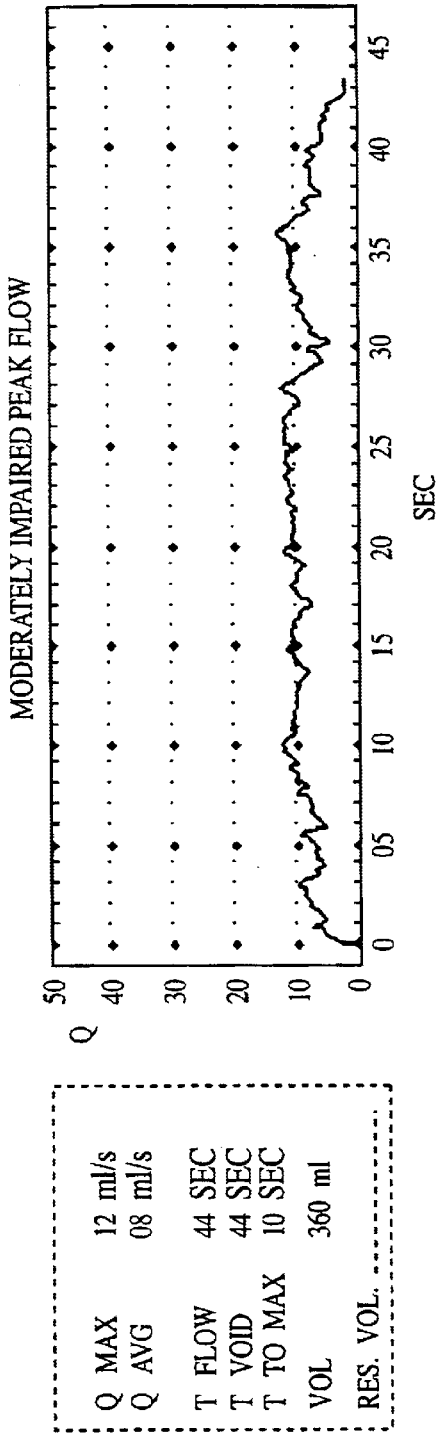

METHODS AND COMPOSITIONS FOR PREVENTING AND TREATING PROSTATE DISORDERS

CROSS REFERENCE TO RELATED APPLICATIONS

This application is a continuation-in-part of Provisional Application Serial No. 60/152,903 filed on Sep. 9, 1999.

FIELD OF THE INVENTION

The present invention generally relates to novel compositions, methods, devices and kits for the prevention and/or treatment of prostate disorders in mammals. The present invention also generally relates to devices for the administration of therapeutic compounds to mucosal membranes in the lower urinary tract of mammals.

BACKGROUND OF THE INVENTION

Diseases of the prostate are common maladies of male mammals, especially men. They include benign prostatic hypertrophy (BPH), carcinoma of the prostate (CaP), prostadynia, prostatitis, and chronic prostatitis.

The steadily increasing age of the world's population is a testament to the success of modem medicine and preventive care. However, this success has brought with it the problem of a greater number of men suffering from BPH, CaP and other prostate disorders.

The incidence of BPH increases steadily with age and is a nearly universal autopsy diagnosis of men in the $8^{th}$ and $9^{th}$ decades of their life (HA Guess, "Epidemiology and natural history of benign prostatic hyperplasia," Urol Clin North Am. 1995; 22:247–261). At least 75% of men over the age of 70 have symptoms consistent with BPH and about 30% of men may have surgery to treat BPH during their lifetime. The Baltimore Longitudinal Study of Aging found that almost 60% of men aged 60 years or older were given a clinical diagnosis of BPH (HM Arrighi et al, "Natural history of benign prostatic hyperplasia and risk of prostatectomy. The Baltimore Longitudinal Study of Aging," Urology 1991; 38 Suppl. 1:4–8). Other mammals that are known to exhibit a high incidence of BPH include dogs and Syrian Hamsters.

Carcinoma of the prostate is now the most common malignancy of men and shows the same pattern of increasing incidence with age as does BPH (SL Parker et al, "Cancer statistics," CA Cancer J Clin 1997; 45:5–27). Indeed, it has been said that every man would develop carcinoma of the prostate (CaP) if he lived long enough.

The bladder serves as a storage vessel for urine produced by the kidneys until the mammal desires to eliminate the urine by voiding. The urethra is a tube or conduit through which urine flows from the bladder to the exterior of the mammal. In man, the urethra is composed of three main divisions—the prostatic, the membranous and the penile segments (FIG. 1).

The prostate gland encases the urethra as it exits the bladder. This anatomical arrangement in which the urethra is completely surrounded by the prostate makes it susceptible to compression by the prostate. Any encroachment upon the lumen of the prostatic urethra will result in obstruction to the flow of urine.

BPH causes obstruction to the flow of urine by two major mechanisms that are distinct components—a static (fixed) component due to the hypertrophied prostate tissue and a dynamic component due to excessive tone in the smooth muscle tissues of the prostate. Both of these mechanisms cause compression and obstruction of the urinary outflow tract. The pathophysiology of BPH involves hypertrophy of the glandular and stromal tissue of the peripheral zone of the prostate and the periurethral area that surrounds the urethra (see FIG. 2) leading to narrowing of the lumen and mechanical obstruction of the urinary outflow tract. Pathology findings on prostate tissue from patients with BPH include fibrosis and hyperplasia of the musculature and gland structure of the prostate.

Patients with BPH commonly complain of symptoms that include difficulty initiating urination (hesitancy), difficulty terminating urination (dribbling), frequent urination secondary to an inability to completely empty the bladder of urine (frequency) and having to awaken in the night to empty the bladder (nocturia). Since no methods are known to prevent or cure BPH, the primary focus of treating BPH is to alleviate these complaints and thereby improve the patient's quality of life.

Two measures of the degree of outflow tract obstruction that are commonly followed in studies of patients with BPH are the subjective complaints of BPH symptoms and measures of the ability to empty the bladder of urine (urodynamics). Urodynamics studies consist of measuring the rate of urine flow and the quantity of urine produced as the patient urinates into a container placed on an electronic scale. A graph of urine flow versus time is produced and the patient's urine flow measurements may then be compared to population derived average urine flow measurements. More complex urodynamics studies measure pressures produced by contraction of the bladder muscles during urination. One measure of the degree of urinary tract obstruction is the maximum or peak urinary flow rate as measured by urodynamics studies. FIG. 3 shows typical urodynamics studies. Peak urinary flow rates of less than 15 milliliters (mls) per second indicate significant urinary obstruction and flow rates of less than 5 mls/second are felt to be an indication for prompt surgical relief of the obstruction.

Prostate specific antigen (PSA) is a serum protease that is widely used as an indicator of disease severity in both BPH and CaP. Not only are prostatic tissues the only source of PSA but serum PSA levels closely correlate with the total amount of prostate tissue present in the body at any given time. Treatments that reduce the tumor mass in CaP or that induce regression of BPH will demonstrate a reduction in serum levels of PSA.

Current medical treatments of BPH include surgery; systemic therapy with alpha-adrenergic blocking agents such as doxazosin, terazosin, prazosin, alfuzosin, R(+)-terazosin, bunazosin, indoramin and tamulosin; alteration of testosterone metabolism; and therapy with an oral herbal medicine extracted from the saw palmetto (Serenoa repens). Huff (U.S. Pat. No. 5,760,054) discloses a number of more specific alpha 1C adrenergic receptor antagonists that may be utilized in the treatment of BPH.

Treatment of BPH with alpha-adrenergic blocking agents is believed to exert beneficial effects by reducing the adrenergic tone of the smooth muscle cells in the prostate via the alpha-1 receptors. Excessive alpha adrenergic tone in the prostatic smooth muscle cells results in a reversible narrowing of the diameter of the urinary outflow tract as it courses through the prostate. This dynamic component of BPH is believed to be the pathophysiology of BPH in men with small prostates. Oral administration of alpha blockers leading to decreased alpha-1 adrenergic tone is felt to result in relaxation of prostatic smooth muscle with a resultant functional improvement in obstructive urinary tract symptoms such as hesitation, dribbling and nocturia. Alpha-adrenergic blocking agents are therefore best used in men with small prostates where smooth muscle contraction is likely to be the primary contributor to the obstructive symptoms. A meta-analysis of placebo-controlled studies of alpha blockers shows improvement in the peak urinary flow rates by 1.5 ml/sec (LM Eri et al, "Alpha-blockade in the treatment of symptomatic benign prostatic hypertrophy," J Urol 1995; 154:923–934).

Another approach taken in the medical treatment of BPH involves altering the metabolism of testosterone. Testosterone is converted by 5alpha-reductase into dihydrotestosterone, a compound that stimulates tissue growth in the prostate. This enzyme exists in at least two isoenzyme forms, Type I and Type II. For reasons that are not known, the ratio of dihydrotestosterone to testosterone present in the blood increases with age. The conversion to dihydrotestosterone greatly increases the potency of testosterone in many tissues including the prostate. The growth of the prostate tissue in BPH is exacerbated by the increased ratio of dihydrotestosterone to testosterone that accompanies aging. Finasteride is a drug specifically developed to block the reduction of testosterone to dihydrotestosterone by 5alpha-reductase. Oral administration of finasteride is approved by the FDA as a treatment for the symptoms of BPH. Finasteride has a gradual onset of action resulting in a 70% reduction in serum dihydrotestosterone levels after daily dosing with 5 milligrams. Administration of finasteride for a period of 6–12 months is generally necessary to determine whether a patient with BPH will improve. Unfortunately, a minority of all patients with BPH improve on oral finasteride and the degree of improvement is relatively small. For example, two large clinical studies demonstrated an increase of only ~1.6 mls/second in peak urinary flow rates with finasteride treatment. Meta-analysis of studies with finasteride demonstrate a 0.5 to 0.8 ml/sec average improvement in peak urinary flow rates compared to placebo (L M Eri et al, "Treatment of benign prostatic hyperplasia. A pharmacoeconomic perspective," Drugs Aging 1997 Febuary; 10(2):107–18).

Another option that may be suggested for men with BPH is an oral herbal medicine preparation extracted from the saw palmetto (Serenoa repens). This preparation contains a variety of compounds that bind androgen receptors and demonstrate 5alpha-reductase inhibition in vitro. The mechanism of action is complex and may involve other pharmacologic activities. Several clinical studies indicate that extracts of Serenoa repens exhibit roughly the same amount of clinical symptom improvement and improvement in peak urinary flow as does finasteride (GS Gerber, "Saw Palmetto in men with lower urinary tract symptoms:effects on urodynamic parameters and voiding symptoms," Urology 1998 June; 51(6):1003–7).

Each of these treatments has limitations and drawbacks. Most of the side effects of medical treatments stem from the systemic (oral) administration of a therapeutic agent to treat a very localized problem in the prostate. The alpha-adrenergic receptor antagonists may cause a significant decrease in the systolic blood pressure, syncope, orthostatic hypotension, asthenia, dizziness, headache, sleepiness, fatigue and impotence. A recent myocardial infarction, transient ischemic attack or cerebrovascular accident constitute relative contraindications to the use of alpha-blockers. The effect of alpha-blockers is usually apparent in the first two weeks of treatment and maximum clinical effects are seen in one or two months (L M Eri et al, Drugs Aging, op cit). Side effects of finasteride administration in men are primarily sexual—erectile dysfunction, decreased volume of ejaculate and loss of libido. Severe teratogenic effects on the fetus preclude the use of finasteride by men whose partner may conceive. Side effects of Serenoa repens therapy are generally the same as with finasteride.

The use of oral therapeutic compounds leads to exposure of all the tissues of the body in an attempt to reach the prostate gland. Local administration of a drug directly to the prostate is hampered by the fact that the prostate gland is an internal organ. The applicant believes that local therapy of the prostate has been achieved to date only by injection of drugs via a hypodermic needle directly into the prostate (A Morales, "Intralesional administration of biological response modifiers in the treatment of localized cancer of the prostate: a feasibility study," Urology 1997 ; 50(4): 495–502). This method of administration is difficult, painful and potentially dangerous.

Administration of therapeutic compounds systemically also has severe drawbacks. Doses in systemic administration are much greater than one might otherwise need if a more direct route of administering drugs were possible. For example, a 40 gram prostate gland in an 82 kilogram (180.4 pounds) man constitutes only 0.05% of the total body mass. Thus, systemic therapy must expose 99.95% of the body to a pharmacologically active drug in order to reach therapeutic levels in the 0.05% of the targeted prostate tissue. Alpha receptors are present diffusely throughout the vascular system and in other organs of mammals. Thus, drugs given to block alpha receptors in the prostate will certainly result in inhibiting normal alpha receptor mediated physiologic functions throughout a mammal. Dihydrotestosterone exerts effects upon most tissues and organs in a male mammal. Thus, reductions in 5alpha-reductase activity systemically must result in other than the desired effects upon the growth of prostatic tissue. Administration of systemic therapy in order to treat the prostate is roughly analogous to painting a house in order to paint the window frame or to spraying a city with pesticides in order to eliminate insects in the city gardens.

Surgical treatment of BPH is the most common surgery of men in the developed countries of the world. In 1989, 400,000 men in the US underwent surgery of the prostate at a cost of greater than $3 billion (M A Kortt et al "The economics of benign prostatic hyperplasia treatment: a literature review," Clinical Therapeutics 1996; 18(6) :1227–1241). The most common prostate surgery involves trans-urethral resection of the prostate (TURP), which is accomplished by resecting the prostatic tissues surrounding the urethra that cause obstruction through a large bore urinary catheter. One prospective randomized study of TURP demonstrated an increase in peak urinary flow of 7.0 ml/sec after surgery (R S Cowles et al "A prospective randomized comparison of TURP to visual laser ablation of the prostate for the treatment of benign prostatic hypertrophy," Urology 1995 August; 46(2):155–600). A second multicenter study demonstrated an increase of 11.35 ml/sec (130%) in peak urinary flow rates following TURP. TURP gives a 4–8 times greater increase in peak urinary flow rates than does treatment with alpha blockers and a 9–22 times greater increase in peak urinary flow rate when compared to finasteride. This surgical procedure carries the usual attendant health risks of a major operation in addition to the complications of urinary incontinence and impotence. Approximately 15% of patients undergoing TURP are estimated to have serious complications and about 5% require a repeat operation after two years. (L M Eri et al, Drugs Aging, op cit). These limitations have spurred the development of a number of other approaches to remove the obstructing tissues with fewer complications such as microwave ablation, cryotherapeutic ablation and laser ablation of the prostate (see M Barba et al, "New technologies in transurethral resection of the prostate," Curr Opin Urol 2000 January; 10(1):9–14; A Koritt op cit and U.S. Pat. No. 6,102,929 as examples). Each new procedure has its individual complications and none has supplanted TURP. The applicant is unaware of any method presently available of treating BPH that can replace surgical removal of the excess prostatic tissue much less prevent the nearly universal development of BPH in aging men.

Thus, there is a pressing need for new and improved methods, compositions and devices to prevent and treat prostate disorders in mammals. Compositions and methods of treatment that exhibit more rapid onset of action, more potent effects on peak urinary flow rates, less systemic side effects, without deleterious effects upon sexual function or urinary continence are needed. Since aging is also associated with increasing incidences of heart attack and strokes, methods of treating BPH that do not exacerbate cardiovascular or cerebrovascular disease are particularly needed. There is also a need for routes of administration for drugs that minimize systemic exposure. There remains a need for compositions and kits useful for preventing and treating prostate disorders in mammals.

SUMMARY OF THE INVENTION

It is one object of the present invention to provide compositions for preventing and/or treating prostate disorders in mammals.

It is another object of the present invention to provide methods for preventing and/or treating prostate disorders in mammals.

It is another object of the present invention to provide devices to deliver therapeutic compounds to the mucosal membranes of the lower urinary tract.

It is another object of the present invention to provide kits for preventing and/or treating prostate disorders in mammals.

These objects have been obtained by the inventor's discovery that administering certain therapeutic compounds to mucosal membranes of the lower urinary tract of a mammal is effective in preventing and/or treating prostate disorders.

The present invention has demonstrated a method of treating BPH with efficacy within one hour of treatment, a surprisingly rapid response compared to weeks or months needed to demonstrate efficacy with present therapies. Further, one treatment has normalized urinary flow in some patients given this therapy. In several cases, the present invention has given improvement in urinary flow rates that exceed reports of improvement with surgery. This invention involves minimal intervention when compared to present therapies and offers hope for the prevention and/or treatment of prostate disorders.

Additional aspects, features, embodiments and advantages of the present invention will be set forth, in part, in the description that follows, or may be learned from practicing or using the present invention. The objects and advantages may be realized and attained by means of the features and combinations particularly pointed out throughout this description and the appended claims. It is to be understood that the foregoing general description and the following detailed description are exemplary and explanatory only and are not to be viewed as being restrictive of the invention as claimed.

BRIEF DESCRIPTION OF THE DRAWINGS

The accompanying drawings, which are incorporated in, and constitute a part of, this specification, illustrate embodiments of the present invention and, together with the description, serve to exemplify the principles of the present invention.

DETAILED DESCRIPTION OF THE PREFERRED EMBODIMENTS

Figure 1A:
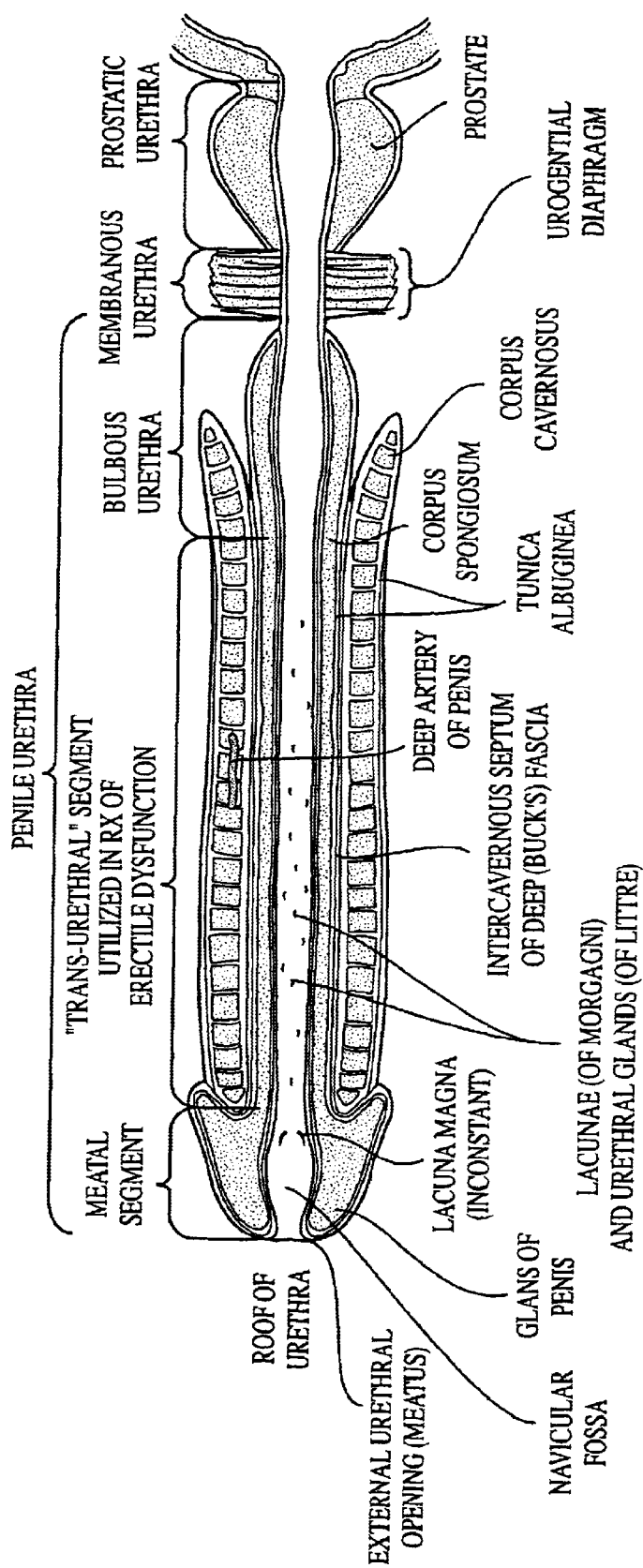
FIG. 1 depicts the anatomy of the male urethra.

All patents, patent applications and publications cited in this description are incorporated herein by reference in their entirety.

Thus, in a first embodiment, the present invention provides novel compositions for the prevention and/or treatment of prostate disorders in mammals.

As used herein, "prostate disorders" refers to benign prostatic hypertrophy (BPH), carcinoma of the prostate (CaP), prostadynia, prostatitis, and chronic prostatitis.

One novel composition comprises a prostaglandin compound and an interferon. Another novel composition comprises meatal suppositories with tocopherol analogs and/or vitamin C analogs. Meatal suppositories containing leuprolide acetate, finasteride and verapamil in a free base form are also believed to be novel. Also believed to be novel are compositions containing an interferon, a 5-alpha reductase inhibitor, chemotherapeutic agents such as tocopherol succinate and vitamin C analogs, muscarinic agents and verapamil.

In a second embodiment, the present invention provides novel methods for the prevention and/or treatment of prostate disorders in mammals comprising administration of one or more therapeutic compounds to the mucosal membrane of the lower urinary tract of the mammal.

In a preferred embodiment, the method for preventing prostate disorders comprises:

a. Identifying the population of mammals at risk of developing a prostate disorder;

b. Performing baseline testing of mammals at risk;

c. Administering one or more therapeutic compound(s) to the mucosal membrane of the lower urinary tract of the mammal; and d. Repeating the baseline testing to evaluate the mammal's response to intervention and to determine whether subsequent interventions should be altered.

When the prostate disorder is BPH, mammals at risk of BPH can be identified (step a) by, for example, evaluating historical factors known to be associated with BPH such as age, race, family history and history of exposure to androgens. Since the strongest factor associated with BPH is age, one may consider every man over a certain age such as 40 to be at risk of developing BPH and a candidate for preventative therapy.

After identifying mammals with BPH, baseline testing (step b) can be performed on, for example, serum PSA, testosterone and dihydrotestosterone levels. A screening urodynamics study with a minimum of peak and mean urinary flow rates can also be performed. Assessment of prostate size by digital exam, ultrasonography, computed tomography or by magnetic resonance imaging may also be used for baseline testing. Symptomatology is determined according to the American Urological Association Symptom Index by inquiring about and recording the following 7 symptoms: sensation of not having emptied the bladder completely after urination; having to urinate again in less than 2 hours after urinating; having to stop and start again several times during urination; difficulties in postponing urination; weak urinary stream; having to push or strain to begin urination; and having to get up at night to urinate (M J Barry et al "The measurement committee of the American Urological Association . . . " J Urol 1992; 148:1549–57).

After conducting the baseline tests, one or more therapeutic compound(s) may be administered to the mucosal membrane of the lower urinary tract of the mammal (step c), preferably utilizing the least invasive method possible. For example, meatal suppositories containing (a) PGEs with or without interferons or (b) 5alpha-reductase inhibitors such as fatty acids, extracts of Serenoa repens or finasteride are suitable for administration. Administration of a suitable dose of the therapeutic agent nightly or every other night is also suitable.

After completing administration of the desired dosage regimen, repeat baseline testing to evaluate the mammal's response to intervention and to determine whether subsequent interventions should be altered (step d) can optionally be carried out by re-evaluating the baseline determinants recorded in step b at intervals of 6 months to 2 years. These determinants preferably consist of at least the symptomatology, the peak urinary flow rate and the PSA level. Improvement in these determinants is desirable and indicates regression of the BPH. Continuation of the intervention used is preferable. Should the individual be without symptoms and possess a normal PSA and Peak flow rate, further improvement in an otherwise normal individual may not be possible. One indication that the intervention used is effective is no progressive increase in PSA, decrease in peak urinary flow or development of symptomatology occurs. In this case, the individual should continue the intervention and be re-evaluated in 6 month to 2 years. If worsening of the symptoms or other indicators occurs, use of higher doses of therapeutic compound(s) may be tried.

When the prostate disorder is CaP, mammals at risk of developing CaP can be identified (step a) by analysis of factors including, but not limited to, family history, race and age. Strongly positive family histories or pathology reports of pre-malignant changes on prostate tissue are indications to initiate preventative therapy. Advanced age is also a strong risk factor for CaP.

After identifying mammals at risk of developing CaP, baseline testing (step b), such as serum PSA and assessment of prostate size by digital exam, ultrasonography, computed tomography or by magnetic resonance imaging may be performed. Available prostate biopsy reports can be studied and new prostate biopsy material obtained at the discretion of the clinician.

After performing baseline testing, one or more therapeutic compound(s) may be administered to the mucosal membrane of the lower urinary tract of the mammal (step c). For example, use of meatal suppositories with (a) prostaglandins with or without an interferon of the alpha or gamma subgroup or (b) tocopherols, vitamin C or retinol or their analogs are suitable for administration to the mammal. Preferably, the prostaglandin is PGA-1, PGA-2, PGJ2, $\Delta^{12}$-PGJ-2, 15-deoxy-$\Delta^{12,14}$-PGJ-2, PGD-2 or 15-deoxy-$\Delta^{12,14}$-PG-2. The therapeutic compound(s) can be administered nightly or every other night.

After completing the administration of the desired dosage regimen, baseline testing for CaP (step d) can be accomplished, for example, by serial PSA determinations or by repeat prostate biopsy.

Methods for treating BPH and CaP preferably comprise
 a. Diagnosing the mammal as having BPH;
 b. Performing baseline testing of the mammal having BPH;
 C. Administering one or more therapeutic compound(s) to the mucosal membrane of the lower urinary tract of the mammal; and
 d. Performing baseline testing to evaluate the mammal's response to the treatment and to determine whether subsequent treatments should be altered.

Performing baseline testing of the mammal and administration of the therapeutic compound(s) are preferably accomplished by the same measures described above in connection with methods for preventing BPH, if the condition is mild. More severe cases of BPH are best treated by administration of one or more therapeutic compound(s) to the prostatic urethra as described below and in the examples. Treatment of local CaP may be effected by administration of chemotherapeutic agents via the prostatic urethra.

As used herein, "therapeutic compound" refers to any therapeutic compound of benefit or potential benefit to prostate disorders. Particularly preferred therapeutic compounds are selected from any of the groups listed below for which non-limiting examples are given:

I. Autocoids and Cytokines such as Prostaglandins and Interferons
II. Chemotherapeutic Agents
III. Alpha-receptor antagonists
IV. Prostaglandin dehydrogenase inhibitors
V. Phosphodiesterase inhibitors
VI. Anticholinergic/antispasmodic agents
VII. Anti-Androgens I. Cytokines
I (A). Prostaglandins Examples of suitable prostaglandins include any natural or synthetic chemical designated to belong to a prostaglandin family, such as PGE-1; PGE-2; PGE-3; PGA-1; PGB-1; PGD-2; 15-deoxy-$\Delta^{12,14}$-PGD-2, PGE-M; PGF-M; PGH-2; PGI-2; 19-hydroxy-PGA-1; 19-hydroxy-PGB-1; PGA-2; PGB-2; 19-hydroxy-PGA-2; 19-hydroxy-PGB-2; PGB-3; 16,16-dimethyl-PGE-1 methyl ester; 15-deoxy-16-hydroxy-16-methyl-PGE-1 methyl ester; 16,16-dimethyl-PGE-2; 11-deoxy-15-methyl-PGE-1; 16-methyl-18,18,19,19-tetrahydrocarbacyclin; (16RS)-15-deoxy-16-hydroxy-16-methyl-PGE-1 methyl ester; (+)-4,5-didehydro-16-phenoxy-tetranor-PGE-2 methyl ester; 11-deoxy-11a, 16,16-trimethyl-PGE-2; (+)-11a,16a,b-dihydroxy- 1,9-dioxo-1-(hydroxymethyl)-16-methyl-trans-prostene; 9-chloro-16,16-dimethyl-PGE-2; arboprostil; iloprost; CL 115,347; 16,16-dimethyl-PGE-2; 15(S)-15-methyl-PGE-2; 9-deoxy-9-methylene-16,16-dimethyl-PGE-2, potassium salt; carbaprostacyclin; prostaglandin D-2; 19(R)-hydroxy-PGE-2; 13,14-dihydro-PGE-1; 11β-PGE-2; 19(R)-hydroxy-PGE-1; 11-deoxy-16,16-dimethyl-PGE-2; PGJ-2; $\Delta^{12}$-PGJ-2; 15-deoxy-$\Delta^{12,14}$-PGJ-2 and semisynthetic or synthetic derivatives of these natural prostaglandins. Cyclodextrin complexes are also included as they may enhance the activity of the solution and stabilize the prostaglandin. Racemic, optically enriched or purified stereoisomers of any of these compounds are also included. Physiologically acceptable salts are also included.

Preferably, the prostaglandin is PGE-1, PGE-2, PGE-3, misoprostol or misoprostanoic acid for the treatment and prevention of BPH. Preferably, the prostaglandin is PGA-1, PGA-2, PGJ2, $\Delta^{12}$-PGJ-2, 15-deoxy-$\Delta^{12,14}$-PGJ-2, PGD-2 or 15-deoxy-$\Delta^{12,14}$-PGD-2 for the treatment and prevention of prostate cancer.

Such prostaglandins are commercially available from Cayman Chemical, Ann Arbor Mich. or described in Alex Gringanz, *Introduction to Medicinal Chemistry*, Wiley-VCH, Inc., New York, pp. 158–159 and 641–642, 1997, which is incorporated herein by reference.

PGE-1, prostaglandin $E_1$, is also known as alprostadil or $PGE_1$. The formal chemical name of PGE-1 is 3-hydroxy-2-(3-hydroxy-1-octenyl)-5-oxocyclopentaneheptanoic acid, and the structure of PGE-1 is

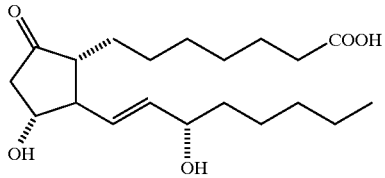

Prostaglandin $E_1$ may be isolated from sheep seminal vesicle tissue as described in Bergstrom et al., *Acta. Chem. Scand.*, vol. 16, p. 501 (1962) and *J. Biol. Chem.*, vol. 238, p. 3555 (1963). The synthesis of prostaglandin $E_1$ may be carried out as described in Corey et al., *J. Am. Chem. Soc.*, vol. 91, p. 535 (1969); Corey et al., *J. Am. Chem. Soc.*, vol. 92, p. 2586 (1970); Sih et al, *J. Am. Chem. Soc.*, vol. 94, p. 3643 (1972); Sih et al., *J. Am. Chem. Soc.*, vol. 95, p. 1676 (1973); Schaaf et al., *J. Org. Chem.*, vol. 37, p. 2921 (1974); and Slates et al., *Tetrahedron*, vol. 30, p. 819 (1974).

PGE-2, prostaglandin $E_2$, is also known as dinoprostone or $PGE_2$. The formal chemical name of PGE-2 is 7-[3-hydroxy-2-(3-hydroxy-1-octenyl)-5-oxocyclopentyl]-5-heptenoic acid, and the structure of PGE-2 is:

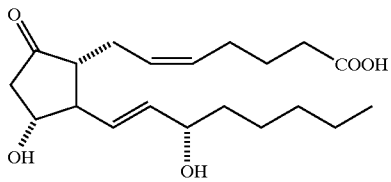

Prostaglandin $E_2$ may be isolated from sheep seminal vesicle tissue as described in Bergstrom et al., *Acta. Chem. Scand.*, vol. 16, p. 501 (1962). Prostaglandin $E_2$ may be synthesized as described in Corey et al., *J. Am. Chem. Soc.*, vol 92, p. 397 (1970); Corey et al., *J. Am. Chem. Soc.*, vol. 92, p. 2586 (1970); and Heather et al., *Tetrahedron Letters*, p. 2313 (1973).

PGE-2 is also commercially available as a Prostin E-2™ suppository and as Prepidil Gel™ from Pharmacia & UpJohn Company, Kalamazoo, Mich., and as Cervidil™ from Forest Pharmaceuticals, Inc., St. Louis, Mo. These preparations are indicated for cervical ripening and contain between 0.5 and 20 mgs of PGE-2.

Misoprostol, also known as 15-Deoxy-16-hydroxy-16-methyl-PGE-1 methyl ester, has the formal chemical name of ( )-methyl-(1R,2R,3R)-3-hydroxy-2-[(E)-(4RS)-4-hydroxy-4-methyl-1-octenyl]-5-oxocyclopentaneheptanoate. Misoprostol (15-Deoxy-16-hydroxy-16-methyl-PGE-1 methyl ester) may be prepared as described in U.S. Pat. No. 3,965,143.

Enprostil has the formal chemical name of [1∀,2∃(1E, 3R*),3∀]-7-[3-hydroxy-2-(3-hydroxy-4-phenoxy-1-butenyl)-5-oxocyclopentyl]-4,5-heptadienoic acid methyl ester. Enprostil may be prepared as described in U.S. Pat. No. 4,178,457.

I (B). Interferons

Interferons are a diverse group of naturally occurring cytokines and immunomodulatory polypeptide agents. Certain interferons are known to exhibit chemotherapeutic effects against certain malignancies, immunosuppressive effects, antiviral effects or antiproliferative effects. Several of this group have been produced by recombinant technology. Interferon alpha-2b from Schering Corporation (Intron A™), interferon alpha-2a from Roche Laboratories (Roferon-A™), interferon beta-1b from Berlex Laboratories (Betaseron™) and interferon gamma-1b (Actimmune™) from Genentech are commercially available agents.

Examples of suitable interferons for use in the present invention include interferon alpha, interferon beta or interferon gamma of natural or synthetic origin that exhibit scar lysis. Specific preferred interferons for use with this invention include any interferon that exhibits the ability to reduce or inhibit the production of fibrous connective tissue, including, but not limited to, interferons of the alpha and gamma sub-groups are preferred. Examples include interferon alpha-2a, interferon alpha-2b and interferon gamma-1b.

II. Chemotherapeutic Agents

Any available chemotherapeutic agents that show activity against prostate carcinoma may be used in the present invention. Agents that demonstrate marked irritation or toxicity to the mucosal surface are to be avoided. Several relatively innocuous agents that demonstrate in vitro activity against CaP cell cultures are readily administered by the present method such as, but not limited to, tocopherols, alpha-tocopherol succinate, vitamin C and analogs, retinol and vitamin A analogs (C Maramag et al "Effect of vitamin C on prostate cancer cells in vitro: effect on cell number, viability and DNA synthesis" Prostate 1997 Aug 1; 32(3): 188–95).

Szarka reviews the strategy of chemoprevention as a possible method of blocking the development of cancers in humans (C F Szarka et al "Chemoprevention of cancer" Curr Probl Cancer 1994 January–February; 18(1):6–79). These strategies center around the systemic administration of agents that have been shown to inhibit the growth of cancer cells in culture. The present invention makes it possible to deliver to the urinary tract sufficient amounts of tocopherols and vitamin C analogs to reach the necessary concentrations demonstrated by the in vitro studies. Systemic administration of these agents does not allow for the delivery of sufficient tissue concentrations to be effective. Concentrations of 1–2 millimolar for ascorbic acid (vitamin C), 0.5 millimolar for alpha-tocopherol and 10 micromolar for alpha-tocopherol succinate are necessary to demonstrate cytostatic or cytotoxic effects on cancer cell cultures. These tantalizing reports must be balanced by the observation that the minimal target tissue concentrations necessary to suppress the development of cancer cells or to kill cancer cells already present in a mammal exceed the maximum levels possible in oral administration by a factor of 10–20 fold for ascorbic acid and by around 7–10 fold for tocopherol. The most potent of these agents is alpha-tocopherol succinate, a succinic acid ester of tocopherol commonly used as a "dry" or solid form of vitamin E in supplements. Oral administration of this most potent antineoplastic agent results in undetectable levels of alpha-tocopherol succinate available systemically due to the rapid hydrolysis of this compound by ubiquitous serum and tissue esterases into alpha-tocopherol and the resultant 50 fold reduction in potency. Suppositories made in Example 10 are 45 mM in alpha-tocopherol succinate or 640 fold greater than the minimally effective concentration. No esterases separate the suppositories from cancerous lesions in the bladder. The present method may be used with any agent that exhibits inhibitory or toxic activity towards cancer cells but is tolerated by normal mucosal cells.

III. Alpha-Receptor Antagonists

Alpha-receptor antagonists including, but not limited to, prazosin, phentolamine, phenoxybenzamine, dibenzamine, doxazosin, terazosin, trimazosin, tolazoline, corynthanine, rauwolscine, tamsulosin and piperoxan, are suitable for use in the present invention.

IV. Prostaglandin Dehydrogenase Inhibitors

By the term "prostaglandin dehydrogenase inhibitor" it is meant any compound which exhibits a significant and selective inhibition of prostaglandin degrading enzyme, or 15-hydroxyprostaglandin dehydrogenase (PGDH). Two forms of 15-hydroxyprostaglandin dehydrogenase (PGDH) are known: Type I, which is $NAD^+$ dependent, and Type II, which is $NADP^+$ dependent. Type I operates at a Km one order of magnitude lower than Type II and is thus more significant physiologically. Type I PGDH is described in Mak et al, *Biochimica et Biophysica Acta,* vol. 1035, pp. 190–196 (1990); Ensor et al, *J. Lipid Mediators Cell Signalling,* vol. 12, pp. 313–319 (1995); and Berry et al, *Biochemical Pharmacology.* vol. 32, no. 19, pp. 2863–2871 (1983), which are incorporated herein by reference. Berry et al., Tai et al., Muramatsu et al., and Mak et al. describe assays for determining enzymatic activity of Type I PGDH as well as methods for determining the degree of inhibition of this enzyme.

Type II PGDH is described in Chang, et al, *Biochem. Biophys. Res. Commun.,* vol. 99, pp. 745–751 (1981); Jarabak, et al, *Prostaglandins,* vol. 18, pp. 241–246 (1979), and Lin, et al, *Biochem. Biophys. Res. Commun.,* vol. 81, pp. 1227–1234 (1978), all of which are incorporated herein by reference.

Examples of suitable 15-hydroxyprostaglandin dehydrogenase inhibitors include, but are not limited to, oleic acid, palmitic acid, sulphasalazine and analogues thereof, 15(R)-prostaglandin E-1, 15(R)-prostaglandin E-2, and 15(R)-15-methyl prostaglandin E-2. U.S. Pat. No. 6,103,765, which provides a more extensive discussion of PGDH inhibitors, is hereby incorporated in its entirety.

V. Phosphodiesterase Inhibitors

Suitable phosphodiesterase (PDE) inhibitors for use in the present invention include, but are not limited to, caffeine, aminophylline, theophylline, amrinone, milrinone, vesnarinone, vinpocetine, pemobendan, cilostamide, enoximone, peroximone, rolipram, R020-1724, zaniprast, dipyridamole, MY5445, IC-351 and sildenafil. Type IV phosphodiesterase inhibitors that selectively block the degradation of cGMP are preferred.

VI. Anticholinergic/Antispasmodic Agents

Anticholinergic agents may induce relaxation in the prostatic smooth muscle when applied by the present method. Suitable anticholinergic agents for use in the present invention include, but are not limited to, atropine, scopolamine, glycopyrrolate, hyoscamine, tolterodine and oxybutynin. Agents that relax smooth muscle such as flavoxate, dicyclomine and calcium channel blockers like verapamil are also of benefit in this method.

VII. Anti-Androgens

Suitable anti-androgens for use in the present invention include, but are not limited to, therapeutic compounds such as finasteride, myristoleic acid, palmitoleic acid, oleic acid, myristic acid, lauric acid, linoleic acid, alpha-linolenic acid, gamma-linolenic acid and extracts of Serenoa repens that block the conversion of testosterone to dihydrotestosterone. Blocking the production of this potent androgen is of particular value in both the treatment and prevention of BPH. Gonadotropin-releasing hormone (GnRH), leuprolide and gonadorelin block the production of testosterone and may be of particular value in treating CaP.

The isolated stereoisomers of any of the above agents may demonstrate improved selectivity of therapeutic action and are included in the scope of this invention.

Any single therapeutic compound or a combination of the above-listed compounds, including combinations of different therapeutic groups, may also be used in the present invention, as long as the therapeutic compounds are physically compatible. Particularly desirable combinations of therapeutic compounds are PGEs and alpha-blockers, PGEs and PGDH inhibitors, and PGEs and interferons.

In some instances, it may be advantageous to pre-treat the mammal with one or more of the therapeutic compounds followed by treatment with one or more of the therapeutic compound. For example, pre-treatment with a PGDH inhibitor followed by treatment with PGE will enhance the efficacy of the present method. Additionally, for example, in the treatment of BPH, the prostatic urethra may be treated with infusion of the prostaglandin solution for 10–30 minutes followed by infusion of the interferon solution.

The therapeutic compounds can be administered in any conventional form, such as a liquid, solid or gel. Examples of suitable liquids include sterile solutions, suspensions, and emulsions, including creams, ointments, and liposomes. Methods for preparing various dosage forms are known, or will be apparent, to those skilled in this art; for example, see Remington's Pharmaceutical Sciences, 18th Ed. (Easton, Pa.: Mack Publishing Company, 1990).

In the case of a solid preparation, the carrier may be any solid substance that is compatible with the drug to be administered, releases the drug upon contact with the mucosa and is not irritating to the mucosa as used. Examples of suitable solids include polyethylene glycol (PEG), polyethylene oxide and other low melting point or water-soluble polymers including fatty acid esters made into suppositories or pellets. Preferred PEG suppositories contain a PEG which is solid at ambient or room temperature but rapidly dissolves/melts when placed on the urethra. Long chained fatty acid triglycerides with or without fatty acid esters are well suited to use with this invention.

Examples of suitable gels include triacetin, hydroxycellulose, gels composed of water, propylene glycol, hydroxypropyl methylcellulose and any other gels which are compatible with the therapeutic agent(s). Liposomal mixtures are particularly preferred when one component is lipid soluble and one component is water soluble. The liposomes may be prepared as either anionic or cationic liposomes depending upon the therapeutic compound to be used. A preferred gel for use with prostaglandins is lecithin organogel prepared according to H. Willimann et al, "Lecithin organogel as matrix for transdermal transport of drugs," *J. Pharm. Sci.,* vol. 81(9), pp. 871–874 (1992). Examples of lipophilic liquids that are particularly preferred are triacetin, tricaprin, tricaproin, tricaprylin and mixtures of various triglycerides.

One may also use a gel in which one or more of the therapeutic compounds is released in a controlled-released manner (i.e., released over time) to prolong the effect of the composition. For example, PGE can be formulated into a cross-linked polyethylene oxide/urethane polymer which is well tolerated by living tissues and releases the prostaglandin in a controlled release manner. Controlled release compositions are disclosed in D. H. Lewis, *Controlled Release of Pesticides and Pharmaceuticals,* Plenum Press, New York, 1981; and A. F. Kydonieus, *Controlled Release Technologies: Methods, Theory, and Applications,* CRC Press, Boca Raton, 1980, which are incorporated herein by reference.

Cyclodextrin complexes of some therapeutic compounds that are lipid soluble may also be used in order to increase the efficacy. For example, cyclodextrin complexes may be prepared by adding the proper stoichiometric ratio of the prostaglandin or other agent to the cyclodextrin in an aqueous solvent and then either using as is or lyophilizing to provide a solid clathrate for mixing. These complexes are described in Yamamura et al, *J. Chromatogr.,* vol. 331, pp. 383–388 (1985); Hirayama et al, *Chem. Pharm. Bull.,* vol. 32 pp. 4237–4240 (1984); Uekama et al, *J. Pharm. Sci.,* vol. 73, pp. 382–384 (1984); and Yamamura et al, *J. Chromatogr.,* vol. 303, pp. 165–172 (1984), which are incorporated herein by reference.

Matrix component(s) that are suitable for use in combination with the therapeutic compound(s) may be composed of any material or mixture of materials that is compatible with the therapeutic compound(s) and that releases the therapeutic compound(s) upon insertion into the meatus or urethra. Specific examples of suitable materials for use as matrix components include but are not limited to fatty acid esters, such as ethyl stearate, methyl stearate, isopropyl stearate, butyl stearate, and cetyl lactate; fatty acid ethers, such as laureth 9; cholesterol esters, such as cholesteryl oleate and cholesteryl palmitate; cholesterol ethers; fatty acid diglycerides; fatty acid triglycerides; fatty acids; phospholipids; glycolipids; and sphingolipids. Ethyl stearate and a mixture of methyl palmitate and tripalmitin are particularly preferred compounds for use as matrix components. Another example of a material suitable for use as a matrix component (s) includes materials such as hydrogels which contain or are saturated with the therapeutic agent(s).

The composition comprising the therapeutic compound(s) of the present invention may be applied by any mode of administration allowing for contact between the composition and the mucosal membranes of the lower urinary tract of a mammal, including, but not limited to, application by way of a catheter, a medicated ring, suppository, dropper, syringe, applicator, tube or by spray. When the composition is a liquid, the administration may be accomplished by means of a dropper, syringe or catheter. When the composition is in the form of a gel, lotion, or cream the administration may be carried out by means of a tube, syringe or catheter. Pharmaceutical compositions that contain the therapeutic compound(s) and are in the form of a solid may be administered by inserting the appropriate amount of the solid dose form directly into the urethra or by use of an applicator.

Figure 1B:
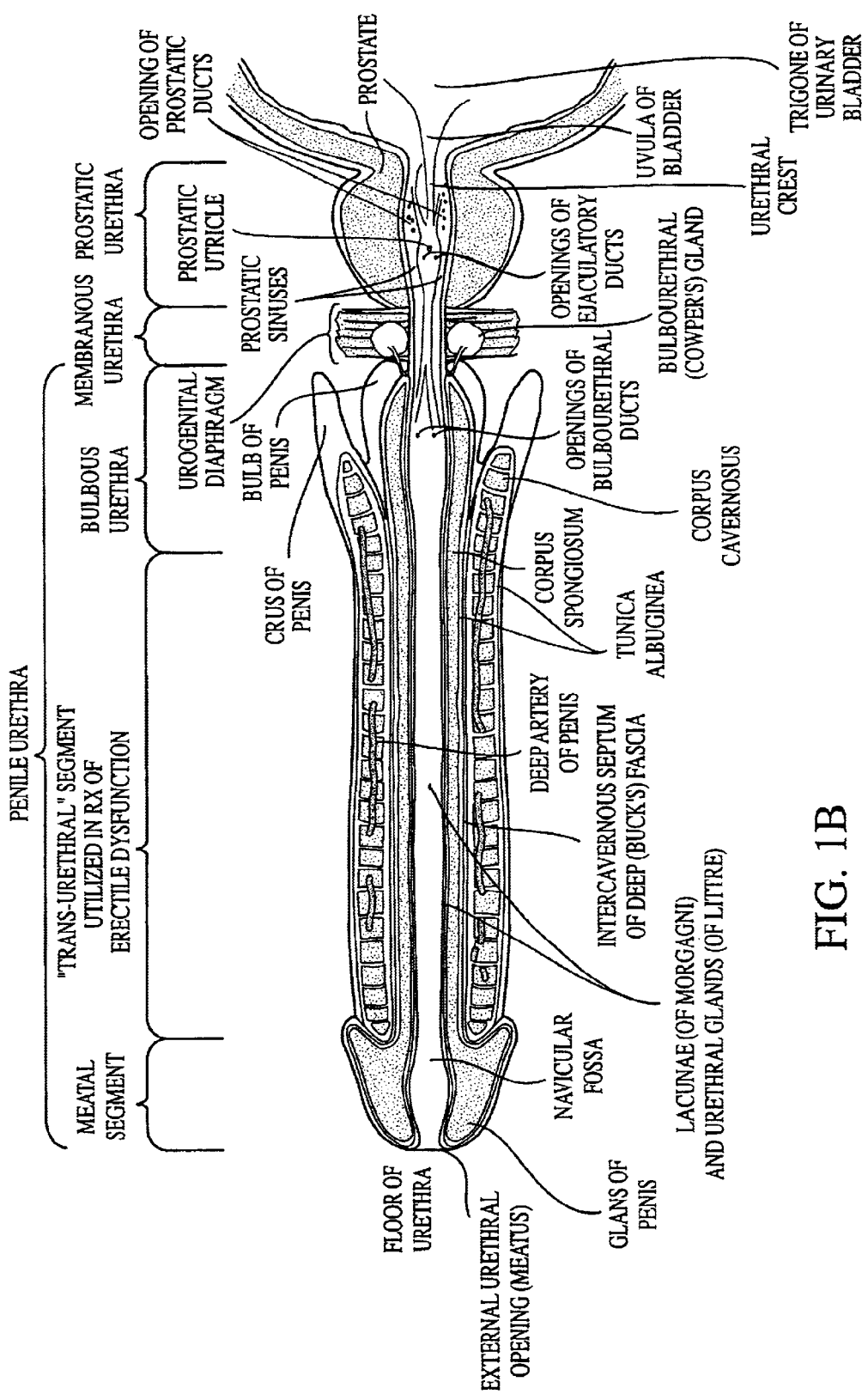
Figure 2:
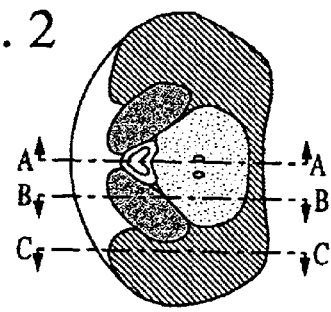
FIG. 2 depicts the anatomical zones of the male prostate.
Figure 2A:
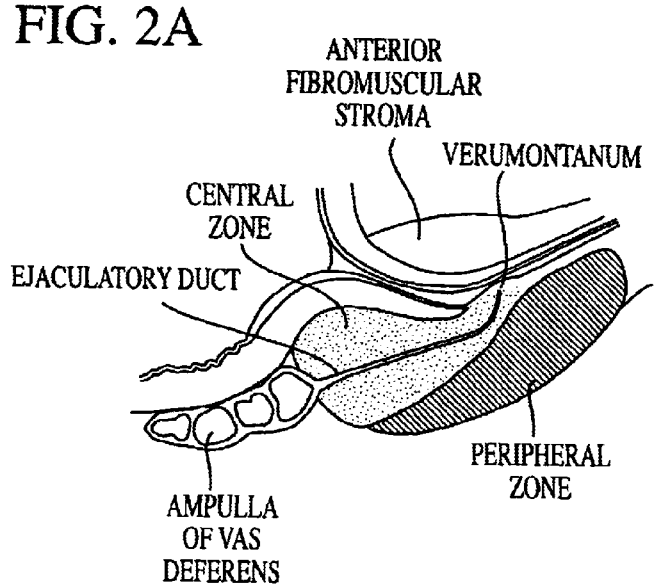
Figure 2B:
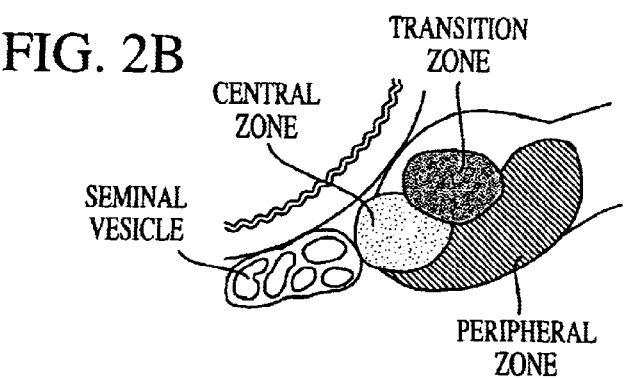
Figure 2C:
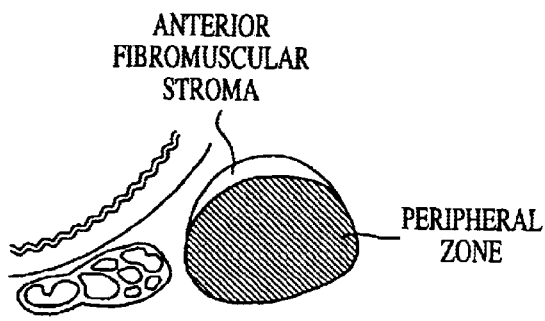

Particularly preferred routes of administration are by application directly to the mucosa of the prostatic urethra and by application to the mucosa of the meatal portion of the penile urethra. As shown in FIG. 1, the male penile urethra consists of three segments: the bulbar urethra, the "trans-urethral" area and the meatal segment. The term prostatic urethral administration as used herein refers to the administration of agents to any portion of the urethra from its origin at the sphincter of the bladder to the membranous urethra. The term meatal administration as used herein refers to the administration of agents to the urethra of the navicular fossa and/or to the penile meatus (as shown in FIG. 1) that are covered by stratified squamous epithelium. Meatal administration is thus essentially the same as topical administration with respect to the difficulty of administering an effective transdermal dose. Meatal administration is considerably easier to carry out than transurethral administration and may be the only possible means of administration in patients with narrowing or scarring of the urethra. The depth of insertion of the suppository in meatal administration is, as measured from the external opening of the penis, generally between 2 mm and 30 mm depending on individual differences. Insertion of a meatal suppository can be easily and painlessly done by simply pressing the end of the suppository into the meatal opening of the penis. No cumbersome devices are required. Those suppositories containing a matrix material that does not melt or dissolve upon insertion are preferably inserted into the urethra to a depth which leaves a portion of the suppository protruding from the urethra, left in the urethra until the desired effect is achieved, and then removed from the urethra by means of the protruding portion.

Figure 4:
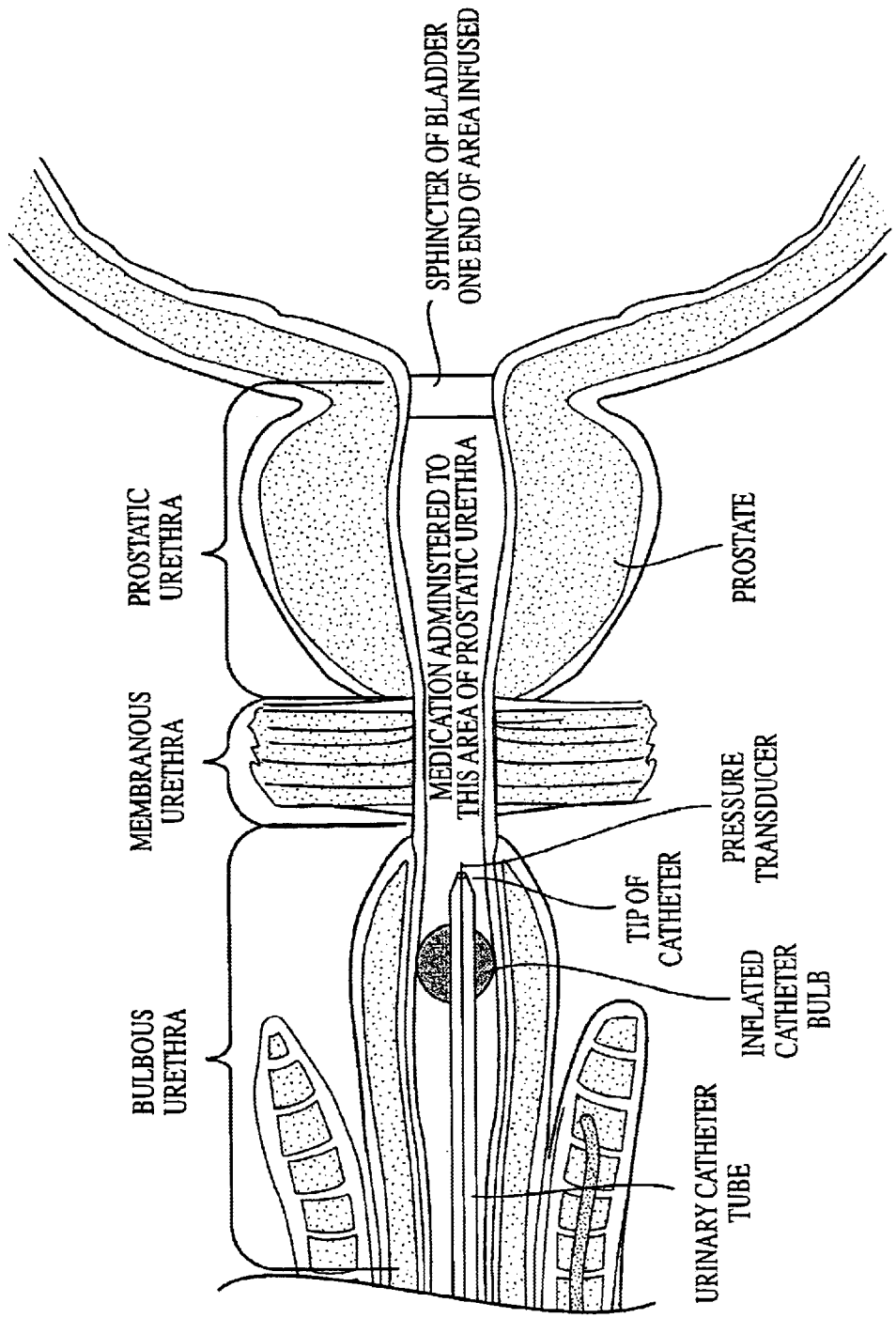
FIG. 4 depicts a method of administration of therapeutic agents via the prostatic urethra.

The therapeutic compounds of the present invention may also be administered to the mucosal membranes of the prostatic urethra by insertion of a small gauge pediatric catheter through the meatus of the glans penis until the proximal portion of the penile urethra or the distal portion of the intramembranous urethra is reached. Gentle inflation of the distal bulb of the catheter affects occlusion of the urethra and affords a direct route via the central channel of the catheter to the prostatic urethra. Infusion of the prostatic urethra with the therapeutic compound (in the form of a solution) is readily performed by retrograde injection of the solution through the tip of the catheter. Contact is maintained with the prostatic urethra by clamping the catheter to prevent the therapeutic solution from refluxing through the bore of the catheter and by the inflated catheter bulb preventing the drug solution from draining down the urethra. The sphincter of the bladder prevents spillage of the drugs into the bladder (FIG. 4). Volumes of 0.5–1.5 mls of solution are well tolerated without leakage of the drug around the inflated bulb of the catheter. Provision for monitoring the pressure in the area of the urethra being treated is made by placing the sensing tip of a pressure transducer into that area through the catheter. This route is quite distinct from the "trans-urethral route" reported by Place in U.S. Pat. Nos. 5,773,020 and 5,919,474 and does not result in undesired side effects such as penile erection. Patients generally report no discomfort and rest or read quietly during the time period over which the catheter is in place. Contact time has varied between 30–180 minutes. The catheter bulb is deflated at the end of the treatment period and the catheter removed. This method is very well tolerated in an outpatient setting and no adverse effects have been seen to date. A number of 3 way catheters are commercially available and may be utilized within the scope of this invention.

Figure 5:
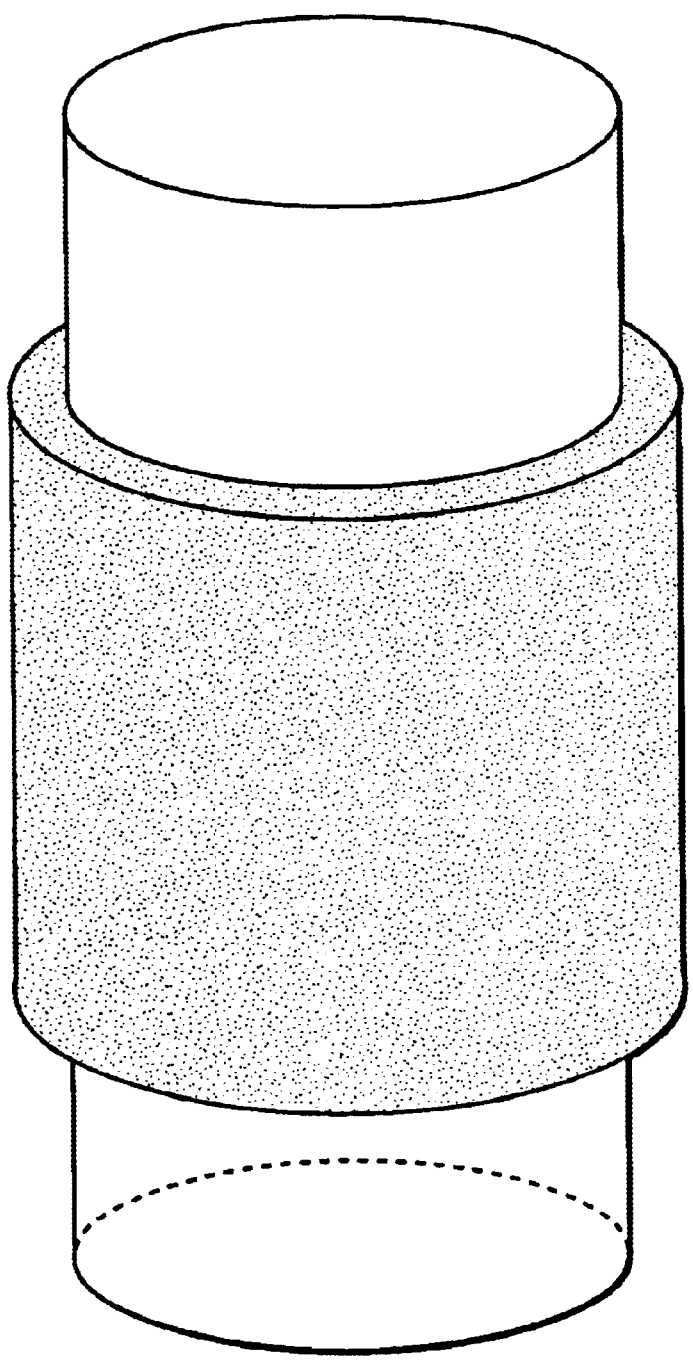
FIG. 5 depicts novel devices for administration of therapeutic agents to the mucosal membranes of the lower urinary tract in mammals.

In a third emodiment, the present invention also provides novel devices for the administration of therapeutic compound(s) to the mucosal membranes of the lower urinary tract. Such devices are constructed of a drug reservoir means that in its simplest form is a ring of material containing the therapeutic compound that is placed in the prostatic urethra. This medicated ring (see FIG. 5) consists of an outer ring of material in direct contact with the prostatic urethral mucosa. This direct contact facilitates drug delivery to the prostate. A central tubular means allows uninterrupted flow of urine from the bladder to the penile urethra.

The ring may be made out of any material that allows release of the drug components, including, but not limited to, hydrogels, high melting triglycerides, polyethylene glycols and polyethylene oxides. Materials that allow timed-release of the therapeutic compound such as a hydrogel are preferred. The ring may be made of a bioerodable material that releases the therapeutic compound as the matrix is eroded or other release mechanisms such as an osmotic pillow that swells upon insertion as it absorbs water from the urethra causing release of a solution of the therapeutic compound(s) through controlled diameter apertures or openings in the outside of the ring. Precautions necessary to prevent the hydrogel from swelling and causing obstruction to the flow of urine include limiting the thickness of the hydrogel ring that is placed in the urethra. Alternatively, a ring composed of methyl palmitate and tripalmitin allows timed-release of the therapeutic compounds without swelling. Provisions may be made for retrieval of the ring should it be necessary due to side-effects in a patient or to terminate the effects (by a means to remove such as a string). Alternatively, the ring may be made to adhere to the outer surface of a urinary catheter in the region that will be in contact with the prostatic urethra. Such a catheter may be inserted into the bladder and left in place to continuously release the therapeutic compounds into the prostatic urethra for as long as several days.

Another variation of this invention is a double lumen catheter device. One lumen would be continuous with the urinary bladder in order to drain urine as it forms. The second lumen would be connected to a pump and drug reservoir on one end and to a fenestrated or multi-channeled opening on the outside of the catheter in contact with the prostatic urethra. This arrangement allows great latitude in controlling dosing and exposure of the prostate to the therapeutic compounds. This arrangement would be of greatest value in the treatment of CaP and severe cases of BPH.

The compositions of the invention may also be administered directly into the glandular ducts of the prostate via cannulation with an endoscopically placed catheter. Gentle infusion of an aqueous solution of therapeutic compound(s) or placement of a suspension of micro particles containing the therapeutic agent(s) would afford either immediate or sustained release of the drugs into the ductal system. All of the above routes are believed to be novel.

The glans penis is derived embryologically from the same tissue as the meatal urethra and is normally covered by the foreskin. Thus, the glans penis may be considered an extension of the distal urethra for the purpose of this invention. Meatal application of the composition for the purposes of this invention may also be achieved by casting the therapeutic agents into a suppository and dispensing the suppository to a patient for use at home. Inserting a suppository trans-meatally is effective in delivering the therapeutic compounds to the prostate. This surprising and totally unexpected result affords a novel route of administering therapeutic compounds to the prostate via a minimally invasive procedure.

The preferred method of administration will depend upon whether the goal of treatment is to prevent or to treat a prostate disorder and upon the severity of the prostate disorder. Preferably, for the prevention of prostate disorders the therapeutic compound(s) is administered by the trans-meatal route, for example with a suppository. Suitable candidates for preventative treatment will be patients who have a strong family history of prostate disorders, patients with early evidence of a progressive decline in the maximum urinary flow rate, patients with early symptoms of BPH and any man over the age of 40 in which the treatment is well tolerated. Meatal suppositories may be dispensed for home use making this route ideal for the administration of therapeutic compounds with minimal expense and intrusion into the patient's life.

In one preferred embodiment, the suppository has a round or pointed tip to facilitate entry into the urethra. Alternatively, the suppository may be tapered along all of or at least a substantial part of its length. The base of the suppository may be distended or flared to provide a built-in stop, so that the depth of the insertion may be determined by the length from the tip of the suppository to the beginning of the flare. Alternatively, the base of the suppository may be attached to a piece of foil, plastic, or paper or attached to the inside of the tip of a condom in order to set the depth of insertion.

Suppositories for use in connection with the present invention will typically have a cross-section having a maximum dimension of from about 1 mm to about 25 mm, preferably from about 2 mm to about 10 mm, most preferably from about 2 mm to about 6 mm, along the portion of the suppository intended to be inserted into the urethra. Although there is in principal no lower limit on the minimum cross-sectional dimension along the portion of the suppository intended to be inserted into the urethra, practically speaking, the suppository should be thick enough to retain sufficient structural integrity to permit insertion of the suppository into the urethra without breaking or significantly bending the suppository. As noted above, the present suppository may have a shape in which the base of the suppository is distended or flared. The distended or flared portion of the suppository will typically have a minimum dimension of at least about 5 mm, preferably at least about 10 mm. Although there is in principal no upper limit on the maximum cross-sectional dimension of the distended or flared portion of the suppository, practically speaking, it is not necessary to make the distended or flared portion any larger than what is required to prevent insertion of the suppository into the urethra beyond the point at which the distended or flared portion begins.

For the treatment of prostate disorders with mild or moderate severity of symptoms, the trans-meatal route is preferable. More severe symptomatology or a desire to see more rapid therapeutic effects would make the route utilizing the prostatic urethra preferable. Administration of therapeutic compounds with a narrow therapeutic index may be most safely administered via the prostatic urethra method under the direct supervision of the physician.

The amount of therapeutic compound(s) to be administered will depend upon the exact size and condition of the patient, the severity of the disorder and the therapeutic compound and method used. The therapeutic compounds of the present invention are to be administered in a therapeutically effective amount, which is understood to mean a nontoxic but sufficient amount of the drug or agent to provide the desired effect. For example, an effective amount means the amount that results in improvement in symptom scores or that results in improvement in peak urinary flow rates or in reduction of the serum PSA level in BPH. A therapeutically effective amount in CaP means, for example, the amount that results in reduction in prostate tumor mass or in reduction in serum levels of PSA.

For example, if the therapeutic compound is a prostaglandin, although the exact amount to be administered will depend on the exact size and condition of the patient, the prostaglandin is suitably administered in an amount of from 1 nanogram to 1,400 micrograms, preferably from 1 microgram to 1,000 micrograms, most preferably from 10 to 500 micrograms. Good results have been obtained with prostaglandin E concentrations in the 100–1,000 mcg per ml range. The broad ranges of suitable dosages reflect clinical findings that various coagents and carriers can either increase or decrease the drug activity exhibited by a given mixture and that individuals may exhibit different levels of sensitivity to a therapeutic agent. In practice, one would begin with a small dosage amount of a therapeutic agent to ascertain the minimum dosage amount needed for an adequate clinical response and increase dosage amount if needed.

The duration of treatment and time period of administration of the therapeutic agent will also vary according to the size and condition of the patient, the severity of the illness and the specific composition and method being used. For example, typically, the prostaglandin will be administered for 30–90 minutes when a catheter based device is used for treatment in a physician's office; for 2–72 hours when a controlled release device is used; and, for several hours when a trans-meatal suppository is used. The administration of the trans-meatal suppository will be terminated by urination. Improvement is surprisingly and unexpectedly rapid with dramatic benefits often seen at the end of one treatment. The number of treatments to be given will depend upon the condition being treated, the severity of the condition and the response of the individual. Excellent responses have been seen with 1–5 treatments applied to either the meatal urethra or the prostatic urethra (see Examples).

If the therapeutic compounds are interferons administered in combination with the prostaglandin, the amount of interferon is suitably administered from 100–50,000,000 IU, preferably from 1,000–10,000,000 IU, most preferably from 100,000–2,000,000 per ml. Although the exact amount of interferon to be administered will depend on the exact size and condition of the patient, good results have been obtained by administration of interferon in the range of 100,000–2,000,000 IU per ml. The corresponding prostaglandin dosage amount is as described above.

Typically, a composition comprising prostaglandin and interferon will be administered for 30–90 minutes when a catheter based device is used; for 2–72 hours when a controlled release device is used; and, for several hours when a trans-meatal suppository is used. The administration of the trans-meatal suppository will often be terminated by urination.

In addition to the therapeutic compound(s) discussed above, the composition administered to the mucosal membrane will typically contain one or more pharmaceutically acceptable carriers (also termed "excipients" or "vehicles") suited to the particular type of formulation, i.e., gel, ointment, suppository, or the like. The vehicles are comprised of materials of naturally occurring or synthetic origin that do not adversely affect the therapeutic compound(s) or other components of the formulation. Suitable carriers for use herein include water, silicone, waxes, petroleum jelly, polyethylene glycol, propylene glycol, liposomes, sugars such as mannitol and lactose, and a variety of other materials, depending, again, on the specific type of formulation used.

It may in some cases be desirable or necessary to include a detergent in the formulation, in an amount effective to increase solubility of the therapeutic compound in the vehicle and bioavailability of the compound following administration. The detergent will typically be a nonionic, anionic, cationic or amphoteric surfactant. In the practice of the invention, the surfactant is selected such that local irritation at the site of administration is avoided. Examples of suitable surfactants include Tergitol.RTM. and Triton-.RTM. surfactants (Union Carbide Chemicals and Plastics, Danbury, Conn.), polyoxyethylenesorbitans, e.g., TWEEN-.RTM. surfactants (Atlas Chemical Industries, Wilmington, Del.), and pharmaceutically acceptable fatty acid esters such as lauryl sulfate and the like.

The formulations may also optionally include one or more components to enhance permeation of the therapeutic compound(s), i.e., "permeation enhancers." Suitable permeation enhancers include those generally useful in conjunction with topical, transdermal or transmucosal drug delivery. Examples of suitable permeation enhancers include dimethylsulfoxide ("DMSO"), dimethyl formamide ("DMF"), N,N-dimethylacetamide ("DMA"), decylmethylsulfoxide ("C.sub. 10 MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone.RTM. from Nelson Research & Development Co., Irvine, Calif.), lower alkanols (e.g., ethanol), SEPA.RTM. (available from Macrochem Co., Lexington, Mass.), and surfactants, including, for example, Tergitol.RTM., Nonoxynol-9.RTM. and TWEEN-80.RTM.

In a forth embodiment, the present invention provides kits to administer therapeutic compounds and novel compositions to the mucosal membranes of the lower urinary tract for the treatment and/or prevention of prostate disorders in mammals. The kits are characterized as containing: (a) a means for containing a therapeutic compound or composition comprising a therapeutic compound and (b) a means for administering the compound or composition to the mucosal membranes of the lower urinary tract of a mammal. When the composition is in the form of a suppository, the means for containing the compound or composition may be foil or plastic wrappers surrounding the suppositories that may be placed into a box or carton or other sealed container. The means for containing the compound or composition may be a bottle, canister or plastic tube when the composition is in the form of a liquid, gel, lotion or cream. Rings or catheters containing the compositions may be placed in individual foil or plastic wrappers and then placed into a box or carton. The means for administering the compound or composition may be a catheter, a medicated ring, suppository, dropper, syringe, applicator, tube or by spray. When the composition is a liquid, the administration may be accomplished by means of a dropper, syringe, catheter or finger tip. When the composition is in the form of a gel, lotion, or cream the administration may be carried out by means of a tube, dropper, syringe, catheter or finger tip. Pharmaceutical compositions that contain the therapeutic compound(s) and are in the form of a solid may be administered by inserting the appropriate amount of the solid dose form directly into the urethra, by the use of an applicator or by the finger tip.

It is to be understood that the means for administering the pharmaceutical composition may be connected to or a part of the means for containing the pharmaceutical composition comprising.

Examples of preferred kits include:
A. A kit which includes a container which can hold 1 to 100 unit doses of the compound or pharmaceutical composition and a dropper which can dispense between 0.1 to 1.0 ml as a unit dose. The container is preferably glass, metal, or a plastic known not to adsorb hydrophobic compounds.
B. A kit which includes a container which can hold 1 to 100 unit doses of the compound or pharmaceutical composition with an applicator to administer the pharmaceutical composition internally onto the mucosal surface. The container is preferably glass, metal, or a plastic known not to adsorb hydrophobic compounds.

C. A kit which includes a tube which holds 1 to 100 unit doses of a compound or pharmaceutical composition, which is in the form of a cream or gel, and an applicator which can dispense a unit dose of the composition.

D. A kit which includes 1 to 100 unit doses of pellets, film or suppositories along with directions for use.

E. A kit which includes 1 to 100 unit doses of urethral rings or catheter devices for administration of the pharmaceutical composition into the prostatic urethra.

The present kits will also typically include means for packaging the container means and the administering means. Such packaging means may take the form of a cardboard or paper box, a plastic or foil pouch, etc. The present kits will also usually include written instructions that describe how to administer the therapeutic compound or pharmaceutical composition containing the therapeutic compound to the mucosa. It is to be understood that the written instructions may be on any of the container means, the administering means, or the packaging means, in addition to being present on a separate piece of paper.

Other features of the present invention will become apparent in the course of the following description of exemplary embodiments which are given for illustration of the invention and are not intended to be limiting thereof.

EXAMPLES

The present invention will be further illustrated in the following, non-limiting Examples. The Examples are illustrative only and do not limit the claimed invention regarding the materials, conditions, process parameters and the like recited herein.

I. Exemplary Formulations

A matrix material for meatal suppositories composed of 12–40% by weight of tripalmitin in methyl palmitate makes a versatile carrier for the therapeutic compound(s) in this method. A meatal suppository may be easily formed by combining 20 grams of tripalmitin with 80 grams of methyl palmitate and melting at 80° C. Lipophillic therapeutic compounds may simply be added to this melted matrix material with stirring and then cast into suppositories by any standard method. Therapeutic compounds that are not lipid soluble may be added in a volatile solvent such as ethanol with stirring and rapidly cast into suppositories. Residual alcohol is removed by application of a vacuum to the solid suppository. Solvents such as 1,2 propanediol may be added to the matrix material to increase the solubility of the therapeutic compound and left as a component of the final product. The co-solvent or volatile solvent to be used may be found by experimenting or by consulting references regarding chemical solubility of a therapeutic compound.

Matrix material with higher proportions of tripalmitin (above 20%) exhibit delayed drug release properties. By the method above, delayed release devices for either meatal or prostatic urethral administration may be easily cast.

In a preferred embodiment, the matrix component is a material or mixture of materials that results in the final composition having a melting point ranging from about 70° F. to about 100° F., preferably from about 70° F. to about 90° F.

Example 1

A base matrix was formed by melting 0.760 grams of tripalmitin and 3.240 grams of methyl palmitate at 80° C. with stirring. This 18% tripalmitin matrix melts and releases any contained therapeutic agent on contact with the warmth of the urethra.

Example 2

To 4.000 grams of the molten matrix from Example 1 was added 4.0 milligrams of PGE-2 with stirring. The solution was drawn into a 2.1 mm diameter rigid tube made of high density polyethylene and allowed to cool to room temperature. One hundred unit doses containing 40 micrograms of PGE2 resulted from cutting the tubing at 12 mm lengths. The outer sleeve of polyethylene was left in place to add strength to the soft meatal suppositories. The suppository is pushed out of one end of the protective sleeve and inserted by hand to use. Any standard method of casting suppositories may also be used. This technique works well with any prostaglandin or other lipid soluble therapeutic compound.

Example 3

To the molten mixture of Example 2 containing tripalmitin, methyl palmate and PGE-2 was added the dry powder from one vial of 25 million IU Intron A™ with rapid stirring. This suspension is rapidly cast into suppositories as in Example 1. One hundred unit doses containing 40 micrograms of PGE-2 and 250,000 IU interferon alpha -2b are thus made. The PGE-2 is rapidly released from the matrix. The solid particles containing interferon alpha-2b are then released by the melting matrix and will slowly dissolve in the moisture of the urinary tract. This simple preparation thus enables the release of the PGE-2 dissolved in the matrix first followed by the suspended interferon particles without the use of a catheter and sequential infusions. The same result may be obtained with any lipid insoluble therapeutic agent that is a solid at room temperature. One may also use the pure interferon powder if available or may substitute a dried liposomal preparation of the therapeutic agent in this method with excellent results. This preferred embodiment may be administered at home by the patient or may be cast as a ring around a catheter by allowing the suspension to cool and solidify around that portion of a catheter that will be in contact with the prostatic urethra.

Example 4

To the molten mixture in Example 1 was added 15 milligrams of prazosin hydrochloride dissolved in ethanol with stirring. The solution was rapidly cast and produced one hundred unit doses containing 150 milligrams of prazosin hydrochloride. The residual ethanol was removed from the suppositories after solidification by vacuum. Any therapeutic agent that is not lipid soluble may be cast into suppositories by selection of a suitable volatile solvent.

Example 5

To a molten mixture 1 gram of tripalmitin and 3 grams of methyl palmitate was added 200 milligrams of oleic acid, 200 milligrams of palmitic acid and 100 milligrams of gama-linolenic acid with stirring until all were dissolved. Casting yielded 100 suppositories containing 2.0 milligrams of oleic acid, 2.0 milligrams palmitic acid and 1.0 milligram of gamma-linolenic acid. Similar preparations made be made with one or a combination of fatty acids. This preparation releases PGDH and 5alpha-reductase inhibitors into the urethra.

Example 6

To the molten matrix of Example 1 was added 5.0 milligrams of finasteride with stirring until dissolved and then cast into one hundred suppositories containing 50 micrograms of finasteride each.

Example 7

Verapamil hydrochloride was dissolved in water and sodium hydroxide solution added until pH 10. The liberated free base verapamil was extracted with chloroform, The chloroform extract was dried over molecular sieves and evaporated to give the pale yellow liquid free base Verapamil. To the molten matrix in Example 1 was added 75 milligrams of Verapamil with stirring and cast to yield one hundred suppositories containing 750 micrograms of Verapamil each. This free base form of Verapamil is absorbed much more rapidly than the available hydrochloride salt from the mucosa of the lower urinary tract. Many therapeutic agents are made into such salts for oral administration. The present invention is best used with either the free base or the free acid form of such agents since the un-ionized form is absorbed more rapidly from a mucosal surface. The alpha blockers and many anti-cholinergic agents listed above may be incorporated by this method.

Example 8

Five milligrams of either tolterodine, oxybutynin, or doxazosin prepared in a free base form as generally described in Example 7 are added in the minimal amount of ethanol to the molten matrix of Example 1 with stirring and cast into one hundred suppositories. The ethanol is removed by vacuum to give unit doses of 50 micrograms of the therapeutic agent.

Example 9

To 4 grams of the molten matrix from Example 1 was added 10 milligrams of free base sildenafil in chloroform with stirring and the mixture was rapidly cast. Removal of solvent gave one hundred suppositories containing 100 microgram doses of sildenafil.

Example 10

To 4 grams of the molten matrix from Example 1 was added 20 milligrams of ascorbyl palmitate and 100 milligrams of alpha-tocopherol succinate in ethanol with stirring and the mixture cast and placed in vacuo to give one hundred suppositories containing 0.2 and 1.0 milligrams respectively of the therapeutic agents. cl Example 11

The formulations of Examples 2–10 may be made by substituting triacetin for the solid matrix material. The resultant liquid preparations may be instilled into the prostatic urethra or applied topically to the glans penis.

Example 12

The formulations of Examples 2–10 may be made by substituting a matrix of 30% tripalmitin and 70% methyl palmitate in order to afford preparations with delayed release properties.

Example 13

The formulations of Examples 2–10 may be made as liposomal preparations as a substitute for the solid matrix. These rapidly bioavailable preparations may be used on any mucosal surface of the urinary tract but will be particularly potent when infused into the prostatic urethra.

II. Subjective Examples

Example 14

A 56-year-old male with a history of BPH, diabetes mellitus and male erectile dysfunction (MED) presented with marked penile deviation from penile nodules (Peyronie's disease) and symptoms of urinary tract obstruction from BPH including hesitancy, decreased urinary force and dribbling. He had a series of nine treatments that entailed insertion of a soft #12 pediatric Foley catheter 8 cm. into the penis, occlusion of outflow from the urethra by constriction with a loose latex band, infusion of a saline solution of PGE2 at pH 6.5 (500 mcg/ml concentration)—total dose 100 mcg PGE2 followed 15 minutes later by 250,000 IU of Intron A (interferon alpha 2b) and allowing 30 minutes for absorption of the treatment. Care was taken to use the minimal amount of compression necessary to prevent leakage of the drug from the urethra so as to not cause is ischemia of the penis.

No adverse effects were seen. The patient experienced immediate and unexpected improvement in his urinary symptoms and marked improvement in erectile function with lessening of the degree of penile curvature over the next 2 weeks, decrease in serum PSA and prolonged beneficial effects months later.

Example 15

A 53-year-old male presented for evaluation of MED. He had had bilateral "penile straightening" surgery 10 years earlier for removal of penile plaques. No plaques were present on exam and the surgical results appeared excellent. Penile ultrasound revealed venous leakage as an etiology of his MED. A 12 French pediatric Foley catheter was placed in the penile urethra and advanced until halted by the massively enlarged prostate gland. The catheter was moved out 5 cm to place the tip roughly before the membranous urethra. Inflation of the catheter bulb with ~1.5 ml of saline to occlude the urethra was accomplished without discomfort (see FIG. 4). The lumen of the catheter was clamped to prevent drainage of the therapeutic agents and infusion of the prostatic urethra with 0.5 ml of normal saline at pH 4.9 containing was accomplished by injecting the solution into the lumen of the catheter proximal to the clamp. The PGE-2 solution was thus delivered through the catheter tip and allowed to remain in place for 30 minutes before infusion of 0.5 ml (5 million IU) of Intron A™. After 30 minutes, the dead volume of the catheter was flushed with 0.5 ml normal saline and treatment continued for 30 minutes before deflating the catheter bulb and removing it. No adverse effects were seen. The patient experienced immediate improvement in his BPH symptoms and improvement from an average urinary flow rat before the $1^{st}$ treatment of 3.5 ml/sec to 30 ml/sec after. He empirically received 2 more treatments at weekly intervals. PSA prior to treatment was 4.0 and after was 2.1 indicating a dramatic reduction in prostate tissue following the therapy. It appears that this result was equivalent to a chemical prostatectomy. His symptoms of BPH and ED cleared totally and he remains asymptomatic almost two years later.

Example 16

Figure 3C:
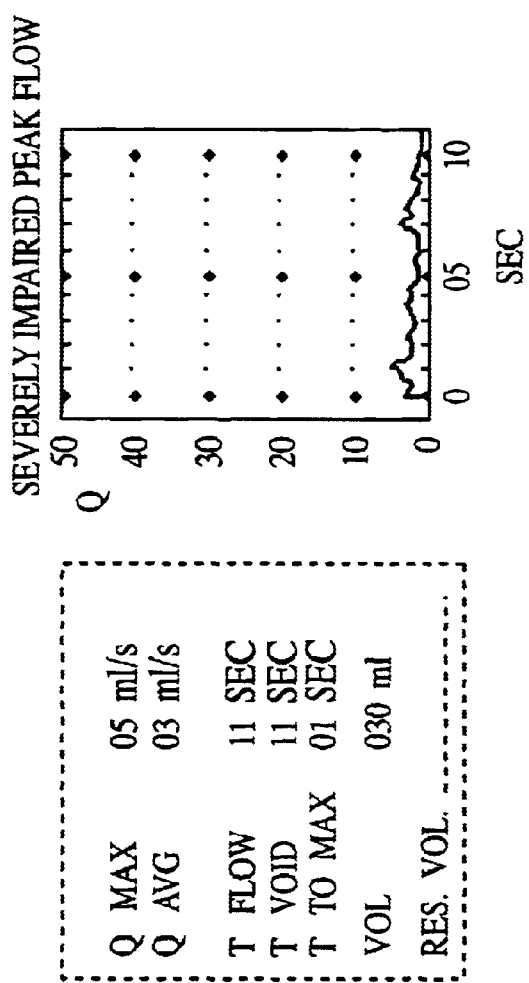
FIG. 3 depicts voiding urodynamics studies.

A 90-year-old male with severe BPH and a number of other medical problems that made him a poor surgical candidate had a pre-treatment PSA of 10.5, prostate biopsies demonstrating only BPH and had urodynamics demonstrating severe obstruction with the peak urinary flow rate of 5 ml/sec and average urinary flow rate of 2 ml/sec prior to treatment (see FIG. 3C). Three treatments as outlined in Example 15 were given without complication. Repeat urodynamics after the $3^{rd}$ treatment showed a peak flow of 8 ml/sec (60% improvement) and an average flow of 4 ml/sec (100% improvement). PSA levels dropped by 32% to 6.8 with some improvement in clinical symptomatology seen. This patient's results are also consistent with a marked reduction in prostate tissue mass induced by the present method and leading to clinical improvement in obstructive symptoms.

Example 17

A 51-year-old male with poorly controlled insulin dependent diabetes mellius, erectile dysfunction, BPH and normal PSA levels (0.3) was given three treatments as outlined in Example 15. FIG. 3B illustrates his urodynamics study just prior to the 1$^{st}$ treatment and FIG. 3A illustrates his repeat study after a single treatment. Peak urinary flow rates more than doubled from 12 ml/sec to 25 ml/sec! Thus, a single 90 minute treatment gave better results than reported with TURP (results in Example 15 were even better). PSA was low at the beginning and remained the same later. The patient resolved all symptomatology of BPH with the three treatments.

Example 18

A 52-year-old male with mild symptoms of BPH was sent home with suppositories made as in Example 3 to insert meatally every 2$^{nd}$ or 3$^{rd}$ night. The patient reported improvement in his symptoms after the 3$^{rd}$ treatment.

Example 19

Men who are at high risk for BPH are given suppositories made as in Example 5 to be inserted in the meatus nightly. It is expected that these men will show a significantly lower rate of development of BPH over the next 5–10 years.

Example 20

Men who are at high risk for CaP are given suppositories made as in Example 10 to be inserted into the meatus nightly or every 2$^{nd}$ night. It is expected that these men will show a significantly lower rate of the development of CaP over the next 5–10 years.

Those skilled in the art will recognize, or be able to ascertain using no more than routine experimentation, many equivalents to the specific embodiments of the invention specifically described herein. Such equivalents are intended to be encompassed in the scope of the following claims.

What is claimed is:

1. A method of treating benign prostatic hypertrophy in mammals, comprising: topical administration, to the urethra or the glans penis, of a therapeutically effective amount of at least one therapeutic compound selected from the group consisting of prostaglandins, interferons, prostaglandin dehydrogenase inhibitors, and phosphodiesterase inhibitors.

2. The method of claim 1, wherein the therapeutic compound is a prostaglandin and an interferon.

3. The method of claim 1, wherein the prostaglandin is selected from PGE-1, PGE-2, PGE-3, misoprostol, misoprostanoic acid, PGA-1, PGA-2, PGJ-2, $\Delta^{12}$-PGJ-2, 15-deoxy-$\Delta^{12,14}$-PGJ-2, PGD-2, and 15-deoxy-$\Delta^{12,14}$-PGD-2.

4. The method of claim 1, wherein the interferon is selected from interferon alpha-2a, interferon alpha-2b, and interferon gamma-1b.

5. The method of claim 1, wherein the phosphodiesterase inhibitor is selected from caffeine, aminophylline, theophylline, amrinone, milrinone, vesnarinone, vinpocetine, pemobendan, cilostamide, enoximone, peroximone, rolipram, R020-1724, zaniprast, dipyridamole, and sildenafil.

6. The method of claim 1, wherein the therapeutic compound is a prostaglandin E and a prostaglandin dehydrogenase inhibitor.

7. The method of claim 1, wherein the therapeutic compound is administered directly to the prostatic urethra by way of a catheter placed in the urethra.

8. The method of claim 1, wherein the therapeutic compound is administered directly to the prostatic urethra by way of a medicated ring or a drug reservoir means.

9. The method of claim 1, wherein the therapeutic compound is administered directly to the meatus or the glans penis in the form of a suppository, solution, gel, or cream.

10. A composition for administration to the urethra, meatus or glans penis for the treatment of benign prostatic hypertrophy, comprising: a therapeutically effective amount of a prostaglandin E compound and an interferon.

11. A composition for administration to the urethra, meatus or glans penis for the treatment of benign prostatic hypertrophy, comprising: a therapeutically effective amount of a prostaglandin E and a prostaglandin dehydrogenase inhibitor.

12. A device for the treatment of benign prostatic hypertrophy that administers a therapeutic compound to the prostatic urethra of a mammal, comprising:

(a) a drug reservoir means, comprising: a therapeutically effective amount of at least one therapeutic compound selected from the group consisting of prostaglandins, interferons, prostaglandin dehydrogenase inhibitors, and phosphodiesterase inhibitors; and, (b) a central tubular means allowing uninterrupted flow of urine from the bladder to the penile urethra.

13. The device of claim 12, wherein the drug reservoir means is a medicated ring comprising: an outer ring of material that is in contact with the prostatic urethra and the therapeutic compound.

14. The device of claim 13, wherein the outer ring comprises a time-release material selected from hydrogels, high melting triglycerides, polyethylene glycols, polyethylene oxides, methyl palmitate, tripalmitin and an osmotic pillow.

15. The method of claim 1, wherein the topical administration is to the glans penis.

16. The method of claim 15, wherein the therapeutic compound is a prostaglandin and an interferon.

17. The method of claim 15, wherein the prostaglandin is selected from PGE-1, PGE-2, PGE-3, misoprostol, misoprostanoic acid, PGA-1, PGA-2, PGJ-2, $\Delta^{12}$-PGJ-2, 15-deoxy-$\Delta^{12,14}$-PGJ-2, PGD-2, and 15-deoxy-$\Delta^{12,14}$-PGD-2.

18. The method of claim 15, wherein the interferon is selected from interferon alpha-2a, interferon alpha-2b and interferon gamma-1b.

19. The method of claim 15, wherein the phosphodiesterase inhibitor is selected from caffeine, aminophylline, theophylline, amrinone, milrinone, vesnarinone, vinpocetine, pemobendan, cilostamide, enoximone, peroximone, rolipram, R020-1724, zaniprast, dipyridamole, and sildenafil.

* * * * *